US012076305B2

(12) United States Patent
Forbes et al.

(10) Patent No.: US 12,076,305 B2
(45) Date of Patent: Sep. 3, 2024

(54) COMPOSITIONS COMPRISING A CONJUGATE OF QUINIC ACID WITH CAFFEIC ACID, COSMETIC AND THERAPEUTIC USES

(71) Applicant: CALSCIENCE INTERNATIONAL LTD, Edinburgh (GB)

(72) Inventors: Iain William George Forbes, Edinburgh Lothian (GB); William Forbes, Edinburgh Lothian (GB)

(73) Assignee: CALSCIENCE INTERNATIONAL LTD, Edinburgh (GB)

( * ) Notice: Subject to any disclaimer, the term of this patent is extended or adjusted under 35 U.S.C. 154(b) by 51 days.

(21) Appl. No.: 15/025,105

(22) PCT Filed: Sep. 19, 2014

(86) PCT No.: PCT/GB2014/052863
§ 371 (c)(1),
(2) Date: Mar. 25, 2016

(87) PCT Pub. No.: WO2015/044649
PCT Pub. Date: Apr. 2, 2015

(65) Prior Publication Data
US 2016/0228394 A1 Aug. 11, 2016

(30) Foreign Application Priority Data

Sep. 30, 2013 (GB) ...................................... 1317286

(51) Int. Cl.
| | | |
|---|---|---|
| A61K 31/216 | (2006.01) | |
| A01N 1/02 | (2006.01) | |
| A61K 8/37 | (2006.01) | |
| A61K 8/9789 | (2017.01) | |
| A61K 8/9794 | (2017.01) | |
| A61K 36/28 | (2006.01) | |
| A61K 45/06 | (2006.01) | |
| A61K 47/55 | (2017.01) | |
| A61Q 7/00 | (2006.01) | |
| A61Q 19/00 | (2006.01) | |
| A61Q 19/06 | (2006.01) | |
| A61Q 19/08 | (2006.01) | |

(52) U.S. Cl.
CPC .......... *A61K 31/216* (2013.01); *A01N 1/0205* (2013.01); *A61K 8/37* (2013.01); *A61K 8/375* (2013.01); *A61K 8/9789* (2017.08); *A61K 8/9794* (2017.08); *A61K 36/28* (2013.01); *A61K 45/06* (2013.01); *A61K 47/55* (2017.08); *A61Q 7/00* (2013.01); *A61Q 19/00* (2013.01); *A61Q 19/06* (2013.01); *A61Q 19/08* (2013.01)

(58) Field of Classification Search
CPC .................................................. A61K 31/216
See application file for complete search history.

(56) References Cited

U.S. PATENT DOCUMENTS

| | | |
|---|---|---|
| 5,395,624 A | 3/1995 | Li et al. |
| 7,968,129 B2 | 6/2011 | Golz-Berner et al. |
| 9,486,400 B2 * | 11/2016 | Osborne ................. A61K 8/97 |
| 2002/0037827 A1 | 3/2002 | Wang et al. |
| 2003/0166567 A1 | 9/2003 | Quirk et al. |
| 2004/0029945 A1 | 2/2004 | O'Brien et al. |
| 2004/0034098 A1 | 2/2004 | Varani et al. |
| 2004/0044000 A1 | 3/2004 | Bunker et al. |
| 2004/0105897 A1 | 6/2004 | Monroe et al. |
| 2004/0116491 A1 | 6/2004 | King et al. |
| 2004/0127420 A1 | 7/2004 | Quirk |
| 2004/0142950 A1 | 7/2004 | Bunker et al. |
| 2004/0167120 A1 | 8/2004 | Klingler et al. |
| 2004/0175349 A1 | 9/2004 | Tsuji et al. |
| 2004/0176393 A1 | 9/2004 | Newton et al. |
| 2006/0074108 A1 | 4/2006 | Gupta |
| 2008/0063693 A1 | 3/2008 | Cook et al. |

FOREIGN PATENT DOCUMENTS

| | | |
|---|---|---|
| CN | 1381236 A | 11/2002 |
| CN | 1839815 A | 10/2006 |
| CN | 101057678 A | 10/2007 |
| CN | 102266318 A | 12/2011 |
| EP | 0 577 516 A1 | 1/1994 |
| EP | 1 283 037 A1 | 2/2003 |
| EP | 2 324 840 A1 | 5/2011 |
| JP | 2006-213636 A | 8/2006 |
| JP | 2010-120908 A | 6/2010 |

(Continued)

OTHER PUBLICATIONS

Facino et al., Echinacoside and Caffeoyl Conjugates Protect Collage from Free-Radical-Induced Degradation: A potential use of Echinacea Extracts in the Prevention of Skin Photodamage, 1995, Planta Med, vol. 61, pp. 510-514 (Year: 1995).*
English Language Machine-Assisted Translation of KR100846125B1 (Published Jul. 8, 2008), 6 pages (Year: 2008).*
Yang et al. Drug Metabolism and Disposition, 2005, vol. 33, No. 7, pp. 930-936 (Year: 2005).*
Xiao et al. Chin. Med. J., 2011, vol. 124, No. 17, pp. 2628-2635 (Year: 2011).*
Lee et al. Pharmacology, 2012, vol. 90, pp. 183-192 (Year: 2012).*
English Language Translation of JP2010120908 (Published Jun. 3, 2010) (10 pages) (Year: 2010).*
Vaalamo, M. et al., "Patterns of Matrix Metalloproteinase and TIMP-1 Expression in Chronic and Normally Healing Human Cutaneous Wounds", British Journal of Dermatology, vol. 135, 1996, pp. 52-59.

(Continued)

Primary Examiner — James D. Anderson
(74) Attorney, Agent, or Firm — ALGM LLP; Harry J. Guttman

(57) ABSTRACT

Use of a composition for the for the prevention, amelioration and/or treatment of disorders and diseases involving cell, tissue or organ senescence, or for the prevention, amelioration and/or treatment of disorders and diseases involving cell, tissue or organ stress caused by an inflammatory process, the composition comprising a conjugate of quinic acid with at least one molecule of caffeic acid, or a derivative, isomer or salt thereof.

22 Claims, 9 Drawing Sheets

(56) References Cited

FOREIGN PATENT DOCUMENTS

| KR | 100846125 B1 * | 7/2008 | |
|---|---|---|---|
| WO | WO-0112178 A1 * | 2/2001 | ........... C07C 69/757 |
| WO | WO 02/47703 A2 | 6/2002 | |
| WO | WO 2006/127525 A2 | 11/2006 | |
| WO | 2016/128745 A1 | 8/2019 | |

OTHER PUBLICATIONS

International Search Report for Application No. PCT/GB2014/052863 dated Mar. 19, 2015, 9 pages.
Agren, M.S., "Matrix Metalloproteinases (MMPs) Are Required For Re-epithelialization of Cutaneous Wounds," Arch. Dermatol. Res., 1999, pp. 291583-291590.
Antognoni, Fabiana et al., "Irbic Acid, a Dicaffeoylquinic Acid Derivative from Cell Cultures", Fitoterapia, vol. 82, No. 7, 2011, pp. 950-954.
Ashworth et al., "Fibrillin Degradation By Matrix Metalloproteinases : Implications For Connective Tissue Remodelling," Biochem Jornal 1999 (340, Part 1): pp. 171-181.
Bellizzi, D. et al., "A Novel VNTR Enhancer Within The SIRT3 Gene, A Human Homologue of SIR2, Is Associated With Survival at Oldest Ages," Genomics, 2005, 85(2), pp. 258-263.
Bolognia, J.L., "Dermatologic and Cosmetic Concerns of the Older Woman", Clin. Geniatr. Med., vol. 9, 1993, pp. 209-229.
Browner, M.F. et al., "Matrilysin-Inhibitor Complexes: Common Themes Among Metalloproteases," Biochemistry, 1995, 34, pp. 6602-6610.
Cheng et al, "Interaction of Sirt3 With OGG1 Contributes To Repair of Mitochondrial DNA and Protects From Apoptotic Cell eath Under Oxidative Stress," Cell Death dis, 2013, p. 4e731.
Dai, Cy et al., "P16ink4a Can Initiate An Autonomous Senescence Program," Oncogene 2000, 19: pp. 1613-1622.
De Fijter, J.W., "Increased Immunogenicity and Cause of Graft Loss of Old Donor Kidneys," J Am Soc Nephrol 2001, 12: pp. 1538-1546.
Donev et al. "Neuronal Death in Alzheimer's Disease and Therapeutic Opportunities," J Cell Mol Med 2009; 13: pp. 4329-4348.
Figueroa et al., "Presenilin-Dependent Gamma-Secretase Activity Modulates Neurite Outgrowth," Neurobiology of Disease, 2002; vol. 9, pp. 49-60.
Gongora, Luis et al., " Effects of Caffeoyl Conjugates of Isoprenyl-Hydroquinone Glucoside and Quinic Acid on Leukocyte Function", Life Sciences, vol. 71, No. 25, Nov. 1, 2002, pp. 2995-3004.
Han, J. et al., "Neuroprotective Effect of 3,5-di-0-Caffeoylquinic Acid on SH-SY5Y Cells and Senescence-Accelerated-Prone Mice 8 Through the Up-Regulation of Phosphoglycerate Kinase-1, Neuroscience", vol. 169, No. 3, 2010, pp. 1039-1045.
Hwang, Y.P. et al., "3-Caffeoyl, 4-Dihydrocaffeoylquinic Acid from Salicornia Hergacea Inhibits Tumor Cell Invasion by Regulating Protein Kinase C-Delta-Dependent Matrix Matalloproteinase-9 Expression", Toxicology Letters, Elsevier Biomedical Press, Amsterdam, NL, vol. 198, No. 2, Oct. 5, 2010, pp. 200-209.
Inoue, T., et al., "SIRT2, A Tubulin Deacetylase, Acts To Block The Entry To Chromosome Condensation In Response To Mitotic Stress," Oncogene 2007, 26(7), pp. 945-957.
Joosten, Sa et al; "Telomere Shortening and Cellular Senescence in a Model of Chronic Renal Allograft Rejection," Amer J Pathol, 2003, 162(4): pp. 1305-1312.
Kong et al, "Sirtuin 3, a New Target of PGC-1a, Plays an Important Role in the Suppression of ROS and Mitochondrial Biogenesis," PLoS One, 2010: 5(7): p. e11707.
Linskens, MH et al., "Cataloging Altered Gene Expression in Young and Senescent Cells Using Enhanced Differential Display," Nucleic Acids Res 1995, 23: 3244-3251.
Liu et al., "Cataloging Altered Gene Expression in Young and Senescent Cells Using Enhanced Differential Display," J. Biol. Chem., 2012; 287: pp. 32307-32311.

Lorenzl, Stefan et al., "Matrix Metalloproteinase-9 is Elevated in 1-Methyl-4-Phenyl-1,2,3.6-Tetrahydropyridine-Induced Parkinsonism in Mice", NeuroMolecular Medicine, Human Press, Inc., vol. 5, 2004, pp. 119-131.
Melk, Anette et al., "Telomere Shortening in Kidneys with Age", J. Am. Soc. Nephrol., vol. 11, 2000, pp. 444-453.
Melk, Anette et al., "Cell Senescence and Its Implications for Nephrology", J. Am. Soc. Nephrol., vol. 12, 2001, pp. 385-393.
Melk, Anette et al., "Increased Expression of Senescence-Associated Cell Cycle Inhibitor P16INK4a in Deteriorating Renal Transplants and Diseased Native Kidney", American Journal of Transplantation, vol. 5, 2005, pp. 1375-1382.
Miyamae, Yusaku et al., "3,4,5-tri-o-caffeoylquinic Acid Inhibits Amyloid Beta-Mediated Cellular Toxicity on SH-Sy5Y Cells Through the Upregulation of PGAM1 and G3PDH", Cytotechnology, vol. 63, No. 2, Mar. 2011, pp. 191-200.
Moses, M.A. et al., "Temporal Study of the Activity of Matrix Metalloproteinases and Their Endogenous Inhibitors During Wound Healing", Journal of Cellular Biochemistry, vol. 60, 1996, pp. 379-386.
North, Brian J. et al., "The Humas Sir2 Ortholog, SIRT2, is an NAD+-Dependent Tubulin Deacetylase", Molecular Cell, vol. 11, Feb. 2003, pp. 437-444.
Outeiro, Tiago Fleming et al., "Sirtuin 2 Inhibitors Rescue a-Synuclein-Mediated Toxicity in Models of Parkinson's Disease", Science, vol. 317, Jul. 27, 2007, pp. 516-519.
Paul, L.C., "Chronic Renal Transplant Loss", Perspectives in Clinical Nephrology, Kidney International, vol. 47, 1995, pp. 1491-1499.
Puangpraphant, Sirima et al., "Dicaffeoylquinic Acids in Yerba Mate (llex paraguariensis St. Hilare) ilhibit NF-[kappa]B Nucleus Translocation in Macrophases and Induce Apoptosis by Activating Caspases-8 and -3 in Human Colon Cancer Cells", Molecular Nutrition & Food Research, vol. 55, No. 10, Oct. 8, 2011, pp. 1509-1522.
Saarilho-Kere, U.K., "Patterns of Matrix Metalloproteinase and TMP Expressing in Chronic Ulcers", Arch. Dermatol. Res., vol. 290, 1998, pp. S47-S54.
Scher, Michael B. et al., "SirT3 is a Nuclear NAD+-Dependent Histone Deacetylase that Translocates to the Mitochondria Upon Cellular Stress", Genes and Development, vol. 21, 2007, pp. 920-928.
Serrano, Manuel et al., "Putting the Stress on Senescence", Current Opinion in Cell Biology, vol. 13, 2001, pp. 748-753.
Sherr, Charles J. et al., "CDK Inhibitors: Postive and Negative Regulators of G1-Phase Progression", Genes & Development, vol. 13, 1999, pp. 1501-1512.
Skjot-Arkil, Helene et al., "Measurement of MMP-9 and—12 Degraded Elastin (ELM) Provides Unique Information on Lung Tissue Degradation", BMC Pulmonary Medicine, vol. 12, 2012, pp. 34.
Stein, Gretchen et al., "Differential Roles for Cyclin-Dependent Kinase Inhibitors p21 and p16 in the Mechanisms of Senescence and Differentiation in Human Fibroblasts", Molecular and Cellular Biology, Mar. 1999, pp. 2109-2117.
Wada, Carol K., "Phenoxyphenyl Sulfone N-Formylhydroxylamines (Retrohydroxamates) as Potent, Selective, Orally Bioavailable Matrix Metalloproteinase Inhibitors", J. Med. Chem., vol. 45, 2002, pp. 219-232.
Database WPI, Week 200720, Thomson Scientific, London GB, AN 2007-193035, XP0027237090.
Database WPI, Week, 200361, Thomson Scientific, London, GB; AN 2003-637335, XP002737091.
Database WPI, Week 201043, Thomson Scientific, London, GB; AN 2010-G03107, XP00273092.
Database WPI, Thomson Scientific, London, GB; AN 2011-Q85864, XP002737093.
Database WPI, Week 200660, Thomson Scientific, London, GB; AN 2006-582266, XP002737094.
Database WPI, Week 200822, Thomson Scientific, London GB, AN 2008-D0339, XP002734649.
English language abstract and machine-assisted English translation for CN 1381236 extracted from espacenet.com database on May 15, 2017, 12 pages.

(56) References Cited

OTHER PUBLICATIONS

English language abstract and machine-assisted English translation for CN 1839815 extracted from espacenet.com database on May 15, 2017, 33 pages.
English language abstract and machine-assisted English translation for CN 101057678 extracted from espacenet.com database on May 15, 2017, 31 pages.
English language abstract and machine-assisted English translation for CN 102266318 extracted from espacenet.com database on May 15, 2017, 16 pages.
English language abstract for EP 0 577 516 extracted from espacenet.com database on May 15, 2017, 2 pages.
English language abstract and machine-assisted English translation for JP 2006-213636 extracted from espacenet.com database on May 15, 2017, 19 pages.
English language abstract and machine-assisted English translation for JP 2010-120908 extracted from espacenet. com database on May 15, 2017, 26 pages.
PCT/GB2016/050316 ISR mailed May 11, 2016, 3 pages.
PCT/GB2016/050316 Written Opinion mailed May 11, 2016, 4 pages.
Battagim et al. (2012) "Comparative study of the effect of green and roasted water extracts of mate (Ilex paraguariensis) on glucosyltransferase activity of *Streptococcus* mutans" Journal of Enzyme Inhibition and Medicinal Chemistry, vol. 27, No. 2, pp. 232-240.
Georgakopoulou et al. (2021) "The bright and dark side of skin senescence. Could skin rejuvenation anti-senescence interventions become a "bright" new strategy for the prevention of age-related skin pathologies?" Mechanisms of Ageing and Development, vol. 193, Article 111409 (14 pages).
Jacobson et al., "Skin changes with aging and disease" Wound Repair Regen. (1996) vol. 4, No. 3, pp. 311-315.
Kumari et al. (2021) "Mechanisms of Cellular Senescence: Cell Cycle Arrest and Senescence Associated Secretory Phenotype" Front. Cell Dev. Biol., vol. 9, Article 645593 (24 pages).
Miyamae et al. (2012) "Protective effects of caffeoylquinic acids on the aggregation and neurotoxicity of the 42-residue amyloid beta-protein" Bioorganic & Medicinal Chemistry, vol. 20, pp. 5844-5849.
Uitto et al., "Proteolytic host cell enzymes in gingival crevice fluid" Periodontology 2000 (2003) vol. 31, pp. 77-104.
U.S. Appl. No. 15/550,388 Restriction Requirement dated May 31, 2018, 7 pages.
U.S. Appl. No. 15/550,388 Response to Restriction Requirement dated Sep. 30, 2018, 5 pages.
U.S. Appl. No. 15/550,388 nonfinal Office action dated Jan. 2, 2019, 15 pages.
U.S. Appl. No. 15/550,388 Response to nonfinal Office action dated May 12, 2019, 9 pages.
U.S. Appl. No. 15/550,388 final Office action dated Aug. 7, 2019, 8 pages.
U.S. Appl. No. 15/550,388 RCE response to final Office action dated Jan. 4, 2020, 13 pages.
U.S. Appl. No. 15/550,388 nonfinal Office action dated Feb. 21, 2020, 6 pages.
U.S. Appl. No. 15/550,388 Response to nonfinal Office action dated May 20, 2020, 10 pages.
U.S. Appl. No. 15/550,388 Notice of Allowance dated May 28, 2020, 7 pages.
U.S. Appl. No. 15/550,388 Notice of Allowance dated Oct. 5, 2020, 7 pages.
U.S. Appl. No. 15/550,388 Corrected Notice of Allowance dated Oct. 29, 2020, 13 pages.
U.S. Appl. No. 15/550,388 Notice of Allowance dated Dec. 8, 2020, 11 pages.

* cited by examiner p65

Pp65

MMP-9 tubulin

COMPOSITIONS COMPRISING A CONJUGATE OF QUINIC ACID WITH CAFFEIC ACID, COSMETIC AND THERAPEUTIC USES

The invention relates to the use of a composition for the prevention, amelioration and/or treatment of conditions associated with the process of senescence and/or inflammation.

The term senescence, including cellular senescence, involves perceptible changes in cells such as the shortening of telomeres, double-strand DNA breaks, an increase in the levels of p16 INK4a and p21, and an increase in the concentration of MMP-9. The process of senescence may be natural, premature, induced or accelerated. Induced or accelerated senescence has been found to be involved in some diseases, and in transplanted cells, tissues and organs. Accelerated senescence has been observed in diseased organs such as the kidney. The natural senescence processes of the skin, as evidenced externally by wrinkles and/or cutaneous pigmented or non-pigmented lesions, can be accelerated by damage produced by ultraviolet radiation from the sun, or by other sources of radiation. In addition, the process of natural senescence may be accelerated by damage to the skin caused by heat, such as burns and scalds.

Sirtuins (SIRTs) are mammalian homologues of the Silent Information Regulator (Sir2) protein found in yeast and are enzymes of class III histone deacetylases (HDACs). Class III HDACs induce transcriptional repression and gene silencing by removal of acetyl groups from histones and regulate gene expression depending on changes in redox and cell metabolism. The Sirtuin 2 (Sir2) family depends on nicotinamide adenine dinucleotide ($NAD^+$) for subsequent reactions, converting acetyl lysine in the presence of $NAD^+$ to O-acetyl-ADP-ribose and nicotinamide. Regulated by the ratio of $NAD^+$ to NADH, the activity of sirtuins varies not only with metabolic changes within the cell but also with a feedback inhibition due to the level of generated nicotinamide.

Seven members of the sirtuin family have been found in mammals and are typically numbered SIRT1 to SIRT7. SIRT1 is mainly localised in the nucleus and has complex roles in cell senescence and tumour suppression by limiting DNA damage by reactive oxygen species and genomic instability. The latter is the subject of current research on cancer cells. SIRT2 is a deacetylase present in the cytosol and is mainly found co-localised with tubulin, which it deacetylates (North, B. J., et al., Mol Cell, 2003, 11(2), 437-44; Inoue, T., et al., Oncogene 2007, 26(7), 945-57). SIRT2 functions as a regulator of mitotic progression and hence the over expression of SIRT2 has been found to delay cell cycle progression. SIRT2 is typically ubiquinated and degraded via the 26s proteasome mechanism. SIRT3 is found in the nucleus and in mitochondria and exerts its function as a deacetylase only after cleavage of its signal peptide. It has been found that SIRT3 expression may be enhanced due to a polymorphism and that the allele lacking this activity is also absent in males over 90 years of age (Bellizzi, D. et al., Genomics, 2005, 85(2), 258-63). This may link the insufficiency of SIRT3 to the process of senescence. SIRT3 is primarily a nuclear enzyme, but is localised to the mitochondria when the cell is stressed or when over expression of the enzyme occurs (Scher, M. B., et al., Genes Dev (2007) 21(8), 920-28). Of the remaining sirtuins, SIRT4 may lack deacetylase activity and is found with SIRT5 in mitochondria. The latter has not as yet been shown to have a precise biological function and is a deacetylase. SIRT6 is located in the nucleus and may be involved in promoting resistance to DNA damage and base pair excision repair. SIRT7 is found in the nucleolus. Depletion of SIRT7 arrests cell proliferation and triggers apoptosis.

The matrix metalloproteinases (MMPs) are part of the family of endopeptidases (proteolytic enzymes) and are distinguished by having a zinc atom associated with three cysteine residues, together with a methionine residue. More than thirty MMPs are present in mammals and are numbered accordingly, for example, MMP-1 (collagenase 1), MMP-2 (gelatinase A) and MMP-9 (gelatinase B). The MMPs are known to hydrolyse large proteins in the connective tissue, degrade large proteins of the extracellular matrix and basal sheets (for example, collagens, gelatins, elastins, proteoglycans and fibronectins) and are expressed at very low levels under normal conditions of organ growth, tissue renewal and regeneration. Under certain conditions in mammals, over expression of MMPs, and in particular MMP-9, may result in disorganisation and/or destruction of the extracellular matrix and/or the spread of cancer. The MMPs are induced by pro-inflammatory cytokines such as tumour necrosis factor-alpha (TNF-alpha) and interleukin-1beta (IL-1beta).

The matrix metalloproteinases are also involved in activating other MMPs and are necessary in the biosynthesis of the key pro-inflammatory cytokine, TNF-alpha. This cytokine can influence the activation of other pro-inflammatory cytokines such as interleukin-1 beta (IL-1 beta) and is of significance in up regulating nuclear factor-kappaB (NF-kappaB). The latter in turn is able to activate MMP-9, therefore creating a self-perpetuating stimulatory pro-inflammatory loop. TNF-alpha is of relevance in a wide range of clinical conditions and diseases and its over expression may be a key contributory factor in several disorders. In addition, TNF-alpha may contribute significantly to downstream effects or events within the cell. Conditions or diseases in which this cytokine has been shown to be over expressed include: autoimmune conditions such as rheumatoid arthritis, chronic obstructive pulmonary disease (COPD), asthma, Multiple Sclerosis, graft rejection, cancer, cachexia (including that of cancer), infectious diseases including tuberculosis and leprosy, radiation (including ultraviolet) damage, anorexia and septic shock.

An over-activity of a matrix metalloproteinase (MMP), or an imbalance between an MMP and the corresponding natural tissue inhibitor of matrix metalloproteinase (TIMP) is associated with the destruction or breakdown of the extracellular matrix in cells and may therefore result in tissue damage, disease or the extension of disease.

Whilst certain MMPs are required for normal embryological development, these enzymes are known to appear and disappear within a strict timeframe, but within a range of concentration. The MMPs, and in particular MMP-9, are over expressed in a range of diseases which are linked both by the direct and downstream effects of these enzymes, for example: diseases of the central nervous system, such as Parkinson's disease, Alzheimer's disease, Multiple Sclerosis, Amyotrophic Lateral Sclerosis and Fragile X Syndrome; Muscular dystrophy, including Duchenne muscular dystrophy and the lower girdle muscular dystrophies; primary human neoplasms and metastasis, for example prostate and breast cancer; alopecia, including areata and totalis; and diseases and conditions associated with inflammatory processes such as acute infections and wound healing. MMP-9 is also found to be present in the dermal papillary fibroblasts.

Certain genetic disorders have been demonstrated to involve an increase in cellular levels of MMP-9. In addition, MMP-9 has been shown to be associated with control of the permeability of the blood brain barrier. MMP-9 also activates alpha-synuclein (a cell protein involved in programmed cell death) by removing a short terminal sequence, resulting in soluble forms and insoluble aggregates of the latter. These insoluble aggregates have been found to be present in Lewy bodies in Parkinson's disease and may lead to apoptosis. Alpha-synuclein is also found in beta-amyloid, a protein of significance in the pathology of Alzheimer's disease. The formation of dopamine from dopa is catalysed by the enzyme tyrosine hydroxylase and the latter enzyme is inhibited by alpha-synuclein. An increase in MMP-9 levels may therefore indirectly affect the levels of dopamine in dopaminergic neurones. Since a cardinal feature of Parkinson's disease is a depletion of dopamine, the over expression of MMP-9 may be of paramount importance in this disease.

MMP-9 has also been found to be an important factor in the spread of cancer, wherein it is involved in altering the milieu surrounding cancer cells such that the cancer cells can more easily invade surrounding tissues. This process typically occurs during extension of the primary tumour, spread to lymph nodes and in metastatic spread to other parts of the body, wherein the cancer cells can flourish and extend their influence.

A number of small non-peptide molecules have been demonstrated to inhibit MMP-9, but so far, these have been of relatively low potency. These molecules include antibiotics such as minocycline, doxycycline and erythromycin. Other low to medium inhibitors of MMP-9 are: arginine, nicotinamide, vitamin D3 and curcumin (from the spice turmeric). However, none of these compounds has been shown to have anti-senescence properties. Efforts have been made to identify highly selective MMP inhibitors having little or no side effects. These highly selective inhibitors of MMPs, particularly of MMP-9, have not previously been shown to have an inhibitory effect on cell senescence. In US 2004/0034098, Varani et al suggest that senescence of human skin can be delayed with the topical application of an MMP inhibitor, preferably a retinoid (which indirectly inhibits MMP). In US 2004/0127420 and US 2003/0166567, Quirk et al disclose peptide inhibitors of MMPs for treating wounds. These inhibitors have sequences related to the cleavage regions of pro-enzyme forms of MMP.

Some publications which refer to inhibition of the matrix metalloproteinases (MMPs) are: Wadda et al., J Med. Chem, 45, 219-232; US 2002/0037827; US 2004/0029945; US 2004/0175349; US 2004/0176393; US 2004/0167120; US 2004/0142950; US 2004/0044000; US 2004/0116491 and US 2004/0105897. The following publications refer to conditions and disorders which may benefit from MMP inhibition: US 2006/0074108; US 2004/0034098; US 2004/0127420; US 2003/0166567; Agren, M. S., Arch. Dermatol. Res., 1999, 291583-291590; Browner, M. F. et al., Biochemistry, 1995, 34, 6602-6610; Moses, M. A. et al., J Cell Biochem., 60, 379; Saarialho and Kere, UK Arch. Dermatol. Res., 1998, 290 (Suppl), 47-54; Vaalamo, M., et al., 1996, Brit. J. Dermatol., 135, 52-59. Although these publications suggest a biological role for these compounds, the precise cellular pathways have not been demonstrated.

The present invention seeks to provide a composition for use in preventing, ameliorating and/or treating conditions which involve the processes of senescence and/or inflammation.

According to the invention, there is provided use of a cosmetic composition for the prevention and/or amelioration of cell or tissue senescence, the composition comprising a conjugate of quinic acid with at least one molecule of caffeic acid, or a derivative, isomer or salt thereof.

In a preferred embodiment, the conjugate is represented by the following formula (I):

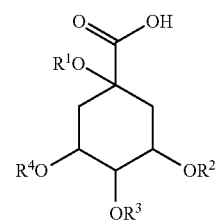

wherein at least one of $R^1$, $R^2$, $R^3$ or $R^4$ is a hydrogen atom; and wherein at least one of $R^1$, $R^2$, $R^3$ or $R^4$ that is not hydrogen is a caffeoyl group, represented by the following formula (II):

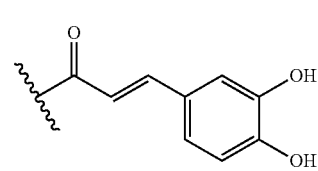

or a derivative, isomer or salt thereof.

Within the context of the present invention, conjugate means a compound formed by the joining together of at least two individual moieties.

In particular, the conjugate is preferably an ester of caffeic acid and quinic acid.

Preferably, in the formation of the conjugate, the hydrogen of $OR^1$, $OR^2$, $OR^3$ and/or $OR^4$ reacts with the carboxylic acid functional group of caffeic acid to form an ester.

By way of example, a typical reaction that may occur to form a conjugate within the context of the invention is shown below:

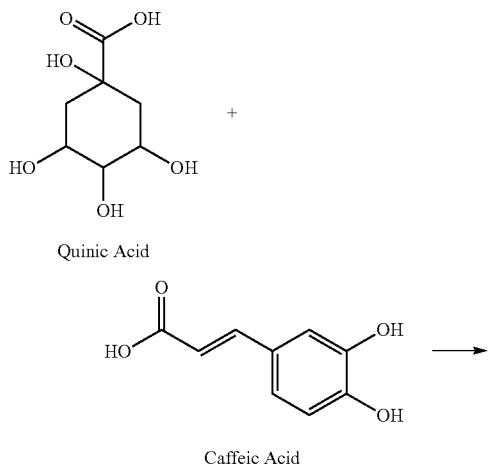

-continued

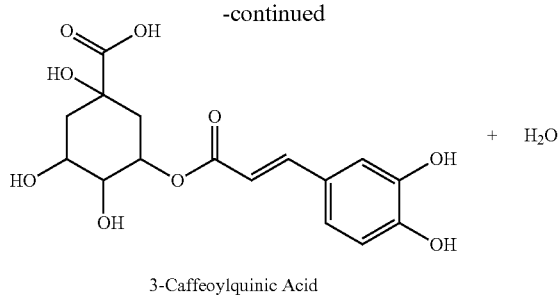

3-Caffeoylquinic Acid

The above example shows the formation of 3-caffeoylquinic acid. The invention is not limited to the use of a composition comprising this conjugate and other conjugates may be used in accordance with the present invention.

Preferably, the cosmetic composition comprises a dicaffeoylquinic acid and/or a tricaffeoylquinic acid, or a derivative, isomer or salt thereof.

Preferably, the conjugate is selected from 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, or 3,4,5-tricaffeoylquinic acid, or a derivative, isomer or salt thereof.

The nomenclature of the dicaffeoylquinic or tricaffeoylquinic acids may be represented as, for example, 1,3-O-dicaffeoylquinic acid or 3,4,5-O-tricaffeoylquinic acid, etc.

In one embodiment, the conjugate is extracted from a natural source. Preferably, the conjugate is a plant extract, preferably an artichoke extract. In another embodiment, the conjugate is synthesised or genetically engineered from plants, bacteria, fungi, mould, algae or another suitable source. Preferably, the composition comprises a plant extract.

In one embodiment, the conjugate further comprise a lipid, fatty acid, alcohol or sugar attachment to another dicaffeoylquinic acid or tricaffeoylquinic acid, or a derivative, isomer or salt thereof.

Preferably, the conjugate comprises at least one acceptable carrier and may be carried within a vesicle, micelle, liposome, nanoparticle or other suitable vehicle.

Typically, the cosmetic composition is applied to the skin. In another embodiment, the cosmetic composition is applied to the hair and/or scalp. Typically, the cosmetic composition may be provided in the form of a serum, lotion, cream, gel, powder, ointment or other medium suitable for the topical administration of the composition to the skin, or for administration to the hair and/or scalp. Typically, cosmetic composition may be administered via a delivery system which may comprise skin cleansers, surfactants, skin conditioning agents, hair conditioning agents, vitamins, hormones, minerals, plant extracts, concentrates of plant extracts, anti-inflammatory agents, anti-oxidants, emollients, moisturisers, skin protectants, skin penetration enhancers, solublizers, and/or pH adjusters.

The term senescence may relate to natural, premature, induced or accelerated senescence.

In a preferred embodiment, the use of the cosmetic composition inhibits the activity of MMP-9. MMP-9 is a collagenase and is associated with the degradation of several components of the skin, such as elastin, gelatine types I and V, collagen type IV and V and fibrillin, which may decrease the elasticity and firmness of the skin. Inhibition of MMP-9 therefore prevents the breakdown of these components and improves skin properties, such as elasticity and firmness.

Advantageously, the use of the cosmetic composition is to enhance extracellular matrix cohesion, preferably of the skin. Advantageously, the use of the cosmetic composition is to stimulate the biosynthesis of fibrillar collagens, elastin and/or fibrillins. Advantageously, the use of the cosmetic composition is to inhibit breakdown of elastin and/or collagenase type IV. Advantageously, the use of the cosmetic composition is to improve skin elasticity and/or skin firmness. Preferably, use of the cosmetic composition is to prevent, ameliorate and/or treat a condition associated a loss of skin elasticity (i.e. to reduce the loss of skin elasticity), for example, as manifested by stretch marks that may be associated with weight loss or pregnancy.

Advantageously, the use of the cosmetic composition is to protect the skin against environmental damage and/or damage caused by ultraviolet radiation, including sun damage. Advantageously, the cosmetic composition improves the natural protective functions of the skin. Advantageously, the cosmetic composition may provide protection against damage caused by factors such as pollution, smoking, and stress.

Preferably, the use of the cosmetic composition is to reduce the formation of wrinkles, reduce skin redness, reduce the appearance of telangiectases, delay the appearance of fine lines, and/or reduce the appearance of dark circles round the eyes.

Thus, use of a cosmetic composition in accordance with the present invention may assist in the prevention and/or amelioration of conditions associated with senescence of the skin, for example, as exemplified by blemishes, thinning of the skin, and/or wrinkling of the skin.

Advantageously, the use of the cosmetic composition is to improve and/or enhance the appearance of the skin.

Preferably, the cosmetic composition is used to prevent and/or ameliorate conditions associated with an excess of subcutaneous fat. Such conditions may be mediated by MMP-9 and may be exemplified by the appearance of dimples on the skin.

In another embodiment, the use of the cosmetic composition assists in the prevention, and/or amelioration of a condition associated with senescence of the hair and/or hair follicles, for example, including a loss or reduction of natural hair colouring, as may be exemplified by greying of the hair. Advantageously, the composition may be used to improve the condition and/or appearance of the hair.

According to a second aspect, there is provided use of a composition for the prevention, amelioration and/or treatment of disorders and diseases involving cell, tissue or organ senescence, the composition comprising a conjugate of quinic acid with at least one molecule of caffeic acid, or a derivative, isomer or salt thereof.

In a preferred embodiment, the composition as used in the second aspect is as defined with respect to the first aspect.

Preferably, the conjugate is represented by the structures shown in formula (I) and formula (II).

In one embodiment, the conjugate comprises an amino acid, peptide, protein, lipid, sugar, polysaccharide, inorganic or organic acid attached to one of the hydroxyl groups. In another embodiment, the conjugate comprises an aryl or alkyl group or alkaline metal attached at position $R^1$, $R^2$, $R^3$ or $R^4$. More preferably, the aryl or alkyl group or alkaline metal is attached at position $R^1$.

In one embodiment, the composition is pyrogen free.

In one embodiment, the conjugate is provided in the form of a free base or a pharmaceutically acceptable salt.

In one embodiment, the conjugate comprises a pharmaceutically acceptable carrier or delivery system which may be in the form of water and oil emulsions, suspensions, colloids, microemulsions, suspensions or emulsions of vesicles, micelles, liposomes, microparticles, nanoparticles, powders or anhydrous compositions. The conjugate may also be coated or combined with a material such as a lipid or sugar, or a combination thereof. The conjugate may be linked to an amino acid, peptide, antibody or other suitable molecule to enable targeting of the conjugate to cells, tissues or organs. In one embodiment, the conjugate is linked to a protein, amino acid, aryl group, alkyl group, fatty acid, sugar, lipid, flavonoid, sugar, salt or ester or other functional group, or an isoform thereof. In one embodiment, the conjugate is linked to a glycine or taurine residue. Preferably, the coating or target-guiding material dissolves to allow efficient and sufficient delivery of the conjugate to the cells, tissues or organs.

The composition may comprise at least one anti-inflammatory agent selected from Boswellia serrata, corosolic acid, ursolic acid, oleanolic acid, salicinol (salacia), rosmarinic acid, ruscogenins, darutoside, asiaticoside, sericoside, harpagoside, horse chestnut (escin, esculin), ginger (gingerol), turmeric extract (tetrahydrocurcuminoids), corydalis, myricetin, artichoke, alfalfa, tea, coffee and/or combinations thereof, or an antioxidant. The composition may comprise a divalent and/or a polyvalent metal ion, for example, copper, zinc, iron, selenium, vanadium or manganese.

In one embodiment, the composition is administered by mouth or by a parenteral route. Typically, the composition may be administered by a dermal, intradermal, transdermal, topical, intramuscular, subcutaneous, intravenous, nasal, oral, sublingual, lingual or rectal route, or by inhalation or instillation. In another embodiment, the composition is administered by incorporation in an implant, or by use of a pumping device. In one embodiment, the composition is administered in an infusion which is circulated through organs, or added to cells, tissues or isolated organs. In a further embodiment, the conjugate is administered in the form of a tablet.

In one embodiment, the composition is administered in combination with an adjuvant, such as an anti-inflammatory drug, an extract or a natural agent. In another embodiment, the composition further comprises an antioxidant, and/or inhibitor of Nuclear Factor-kappaB (NF-kappa B), or an inhibitor of a matrix metalloproteinase (MMP), or an antibiotic or vitamin, for example, vitamin D, vitamin D3, vitamin C dehydroascorbate, vitamin B, vitamin E, or other suitable vitamin and/or co-factor.

In one embodiment, the composition is incorporated within a food or drink.

Advantageously, the composition may be used for the prevention, amelioration and/or treatment of a disorder or disease associated with an increase in the expression of the sirtuin 2 gene or protein, and/or a decrease in expression of the sirtuin 3 gene or protein.

Advantageously, the composition is capable of activating the expression of the sirtuin 3 gene to enhance the production of the sirtuin 3 protein. Advantageously, the composition is capable of inhibiting the expression of the sirtuin 2 gene to inhibit the production of the sirtuin 2 protein. A reduced level of SIRT3 in cells and tissues is thought to be a marker of senescence.

Advantageously, the composition is capable of inhibiting the expression of the p16INK4a gene in cells, tissues or organs, for example, following oxidant challenge.

Advantageously, use of the composition may inhibit the up regulation of SIRT2 which occurs in neurodegenerative and other diseases of the nervous system. Preferably, the composition may be used to prevent, ameliorate and/or treat neurotoxic effects caused by the up regulation of alpha-synuclein in neurodegenerative and other diseases of the nervous system.

Preferably, use of the composition inhibits key pro-inflammatory cytokines, for example, interleukin-1 beta (IL-1 beta), interleukin-6 (IL-6), tumour necrosis factor alpha (TNF-alpha), the chemokine interleukin-8 (CXCL-8; IL-8) and interferon-gamma (IFN-gamma) in cells tissues or organs.

In one embodiment, use of the composition modulates expression of the product of the Human Protection of Telomeres 1 (hPOT1) gene. Such modulation indicates a significant protective effect on telomeres which under normal circumstances shorten with oxidant challenge.

Advantageously, the composition may be used to inhibit MMPs, NF-kappa B and senescence-associated genes.

In one embodiment, the composition is used for the prevention, amelioration and/or treatment of senescence associated degeneration in stem cells, or in cells of the nervous system, skin, tissues or organs, wherein the senescence may be induced by natural factors, or wherein the senescence may be accelerated. Typically, accelerated senescence may be caused by exposure to radiation or chemotherapy; a genetic abnormality such as in progeria or associated disorders; disease; or the transplantation of cells, tissues or organs. In one embodiment, the composition is used for the prevention, treatment and/or amelioration of senescence (for example, accelerated senescence) which may occur in transplanted cells, tissues or organs, such as the kidney. The cells, tissues or organs for transplantation purposes may be autologous, or may be obtained by cloning, laboratory manufacture, industrial manufacture, or from a mammalian source.

In one embodiment, the composition is used for the reversal of senescence-associated degeneration of cells, including stem cells and cells of the nervous system, tissues and/or organs.

Preferably, the composition is also used for the prevention, amelioration and/or treatment of a condition associated with accelerated senescence in diseased or transplanted tissues or organs, or in transplanted or infused cells including bone marrow, stem cells, red or white blood cells, cell lines, and/or in stored organs for transplantation.

In another embodiment, the composition is used for maintaining or extending the viability of organs or cells, including stem cells, before and/or after the process of transplantation, and/or in cell lines.

In one embodiment, the composition is used for the prevention, amelioration and/or treatment of a disorder or disease associated with the immune system.

In one embodiment, the composition is used for the prevention, amelioration and/or treatment of a skin disorder or disease.

In another embodiment, the composition is used for the prevention, amelioration and/or treatment of a disorder or disease associated with senescence of the hair or hair follicles. Typically, the composition may be used for the prevention, amelioration or treatment of a disorder or disease associated with hair loss or damage to hair follicles, thinning of hair, or alopecia. Preferably, the composition is applied to the hair in the form of a spray, cream, lotion or serum.

In a further embodiment, the composition is used for the prevention, amelioration and/or treatment of a pathological disorder associated with senescence of cells or tissues.

In yet another embodiment, the composition is used for the prevention, amelioration and/or treatment of a disorder or disease associated with the kidney, lung, liver, heart and/or pancreas. In one embodiment, the composition may be administered in combination with an adjuvant.

Preferably, the composition is used for the prevention, amelioration and/or treatment of a condition associated with neurodegeneration.

In one embodiment, the composition is used for the prevention, amelioration and/or treatment of senescence occurring in cells of the nervous system, including neurones, astrocytes, oligodendrites, glial cells, Schwann cells and cells of the blood brain barrier. In another embodiment, the composition is used for the prevention, amelioration and/or treatment of disorders or diseases of the central and/or peripheral nervous system. Preferably, the composition is used for the prevention, amelioration and/or treatment of Alzheimer's disease, Parkinson's disease, Multiple Sclerosis, Amyotropic Lateral Sclerosis, Fragile X Syndrome and/or Charcot-Marie-Tooth Syndrome.

In another embodiment, the composition is used for the prevention, amelioration and/or treatment of a condition associated with senescence of the ear, such as deafness, loss of hair cells from the inner ear or tinnitus; a condition associated with senescence of the eye, such as macular degeneration, cataract or glaucoma; osteoporosis; osteoarthritis; intervertebral disc degeneration; type 2 diabetes; prostate hypertrophy and/or emphysema.

In another embodiment, the composition is used for the prevention, amelioration and/or treatment of diseases of the cardiovascular system.

In a further embodiment, the composition is used for the prevention, amelioration and/or treatment of a condition associated with senescence in endothelial cells, or in the prevention, amelioration and/or treatment of a condition associated with senescence in hepatic cirrhosis.

In a further embodiment, the composition is used for the prevention, amelioration and/or treatment of mitochondriopathies, including the neuromitochondriopathies. Advantageously, the composition may contribute to repair of mitochondrial DNA by up regulating sirtuin 3 and thus encouraging the interaction of sirtuin 3 with 8-oxoguanine-DNA glycosylase (OGG1), a DNA repair enzyme.

Typically, the composition may be capable of maintaining structural integrity against possible enzymatic attack in the alimentary tract, plasma, the liver and/or other organs.

In one embodiment, the composition is manufactured in a laboratory or on an industrial scale by solid-phase synthesis or other means, and may be purified to provide a therapeutically effective dose of the composition.

Advantageously, the composition may be used in human therapeutics and/or in veterinary practice, and is typically administered to a mammalian subject.

Advantageously, the composition may be administered with a high degree of safety.

According to a third aspect, the invention relates to use of a composition for the prevention, amelioration and/or treatment of disorders and/or diseases involving cell, tissue or organ stress caused by an inflammatory process, the composition comprising a conjugate of quinic acid with at least one molecule of caffeic acid, or a derivative, isomer or salt thereof.

Preferably, the composition as used in the third aspect is as defined with respect to the first and second aspect.

Preferably, the conjugate is represented by the structures shown in formula (I) and formula (II).

Preferably, the composition is used for the prevention, amelioration and/or treatment of disorders or diseases associated with an increase in the expression of one or more matrix metalloproteinase (MMP) genes and/or proteins. In a preferred embodiment, the composition inhibits MMPs, NF-kappa B, cytokines and/or tissue inhibitors of matrix metalloproteinase (TIMP) activators. These factors are known to be involved in the process of inflammation. In one embodiment, the disorder or disease is associated with an increase in the expression of MMP-9 and/or MMP-2. Typically, the composition inhibits MMP-9 and/or MMP-2.

In one embodiment, the composition is used for the prevention, amelioration and/or treatment of a malignant or benign neoplasm. Preferably, the malignant neoplasm may be associated with breast, lung, colon, rectum, prostate, blood cells, oral cancer, skin cancer or melanoma or leukaemia.

Preferably, the composition is used for the prevention, amelioration and/or treatment of the spread of cancer cells (for example, metastasis), including the local invasion of surrounding tissues, and their dissemination to other tissues and/or organs. Typically, the composition may be used for the prevention, amelioration and/or treatment of lymphatic, capillary, venous or arterial invasion by cancer cells, including spread to lymph nodes.

In one embodiment, the composition is used in combination with another anti-cancer therapy including chemotherapy, synergistic compounds, antibodies, genes, gene products, cell therapy and/or radiation.

In another embodiment, the composition is used for the prevention, amelioration and/or treatment of hypertrophy or hyperplasia of the prostate gland. In one embodiment, the composition is administered in combination with another agent, for example, an adjuvant.

In one embodiment, the composition is used for the amelioration and/or treatment of chronic inflammatory disease of the breast, or polycystic disease including polycystic disease of the ovary or kidney.

In another embodiment, the composition is used for the prevention, amelioration and/or treatment of endometriosis, including the local invasion, infiltration and/or spread of endometrial cells into the walls of the uterus, surrounding tissues and organs.

In yet another embodiment, the composition is used for the prevention, amelioration and/or treatment of adhesions following a surgical or medical procedure.

In one embodiment, the composition is used for the prevention, treatment and/or amelioration of obstruction of the fallopian tubes or ducts of the male reproductive organs following an inflammatory reaction.

In one embodiment, the composition is used for the prevention, amelioration and/or treatment of periodontitis and/or gum retraction. In this embodiment, the composition is preferably administered by an oral route, which may involve the use of a gel, spray, toothpaste and/or mouthwash.

In another embodiment, the composition is used for the prevention, amelioration and/or treatment of disease of the haemopoietic system, such as primary and secondary haemophagocytic lymphohistiocytosis (HLH) or Langerhan's cells histiocytosis (LCH).

Preferably, the composition is used for the prevention, amelioration and/or treatment of disorders and diseases of muscle, including muscular dystrophy or muscle injuries. In one embodiment, the composition is used for the prevention, amelioration and/or treatment of Duchenne muscular dystrophy, lower-girdle muscular dystrophy and/or dystroglycanopathies. Advantageously, the composition may be used for the promotion or regeneration of skeletal muscle fibres and/or to increase the numbers and biological activation of satellite cells or stem cells.

In another embodiment, the composition is used for prevention, amelioration and/or treatment of muscular dystrophies or other genetic or epigenetic disorders associated with the deacetylation of genes by a mammalian histone deacetylase (i.e. a member of the Sirtuin family).

Preferably, the composition is used for the prevention, amelioration and/or treatment of Alzheimer's disease, Parkinson's disease, Multiple Sclerosis, Charcot-Marie-Tooth Syndrome, Huntington's disease, motor neurone disease, or a disease of the central or peripheral nervous system in which a cellular tissue inflammatory reaction is involved.

In another embodiment, the composition is used for the prevention, amelioration and/or treatment of injuries to tissue of the nervous system including those of the brain, spinal cord and/or peripheral nerves. Preferably, the composition is used for the prevention, amelioration and/or treatment of conditions associated with stroke, including multi-infarct syndrome.

In another embodiment, the composition is used for the prevention, amelioration and/or treatment of conditions associated with an increased permeability of the blood brain barrier.

In one embodiment, the composition is used for the prevention, amelioration and/or treatment of fatigue, including chronic fatigue syndrome, post-viral fatigue or fatigue associated with cancer.

In another embodiment, the composition is used for the prevention, amelioration, and/or treatment of diseases of the eye, including uveitis, conjunctivitis, corneal opacities and/or dry eye. In one embodiment, the composition may be administered in combination with an adjuvant treatment.

In a further embodiment, the composition is used for the prevention, amelioration and/or treatment of diseases of the cardiovascular system, including atherosclerosis, arteriosclerosis, aneurysms, coronary heart disease and the stabilisation of carotid plaques.

In another embodiment, the composition is used for the prevention, amelioration and/or treatment of a condition associated with an increase in the levels of low density lipoproteins. In a further embodiment, the composition is used for reducing the level of low density lipoproteins in blood, body fluids, cells, tissues and organs.

In another embodiment, the composition is used for the prevention, amelioration and/or treatment of a condition associated with the use of arterial or venous stents.

In another embodiment, the composition is used for the prevention, amelioration and/or treatment of inflammatory disorders of the respiratory system including chronic obstructive pulmonary disease (COPD), bronchiectasis and/or chronic bronchitis.

In one embodiment, the composition is used for the prevention, amelioration and/or treatment of inflammatory diseases of the bowel, including irritable bowel disease, Crohn's disease or ulcerative colitis. Advantageously, the invention may be used for the prevention, amelioration and/or treatment of pseudomembranous colitis which may be caused by *Clostridium difficile* infection.

In another embodiment, the composition is used for the prevention, amelioration and/or treatment of a condition associated with injury to joints, tendons, synovial membrane and/or cartilage. Preferably, the composition is used for the prevention, amelioration and/or treatment of arthritis, including rheumatoid arthritis and/or osteoarthritis.

In one embodiment, the composition is used for the prevention, amelioration and/or treatment of immune or autoimmune diseases, including systemic lupus erythematosus (SLE), discoid (cutaneous) and/or neonatal lupus.

Advantageously, the composition may be used for the prevention, amelioration and/or treatment of acute or chronic inflammatory conditions which may be induced by disease or injury.

Advantageously, the composition may be used to inhibit analogues, orthologues, homologues, derivatives and variants of MMPs, preferably MMP-9. The MMP-9 which is inhibited preferably comprises a functional metal cation in the catalytic active site and has the ability to hydrolyse polypeptides. Advantageously, the composition may inhibit full-length mammalian matrix metalloproteinases (MMPs), or truncated forms of MMPs, or a catalytic domain from these enzymes which comprises a metal cation.

Variations and modifications of the invention are included within the scope of the invention and will be understood by those skilled in the art.

The invention will be further described by way of example and with reference to the following figures, in which.

Figure 1:
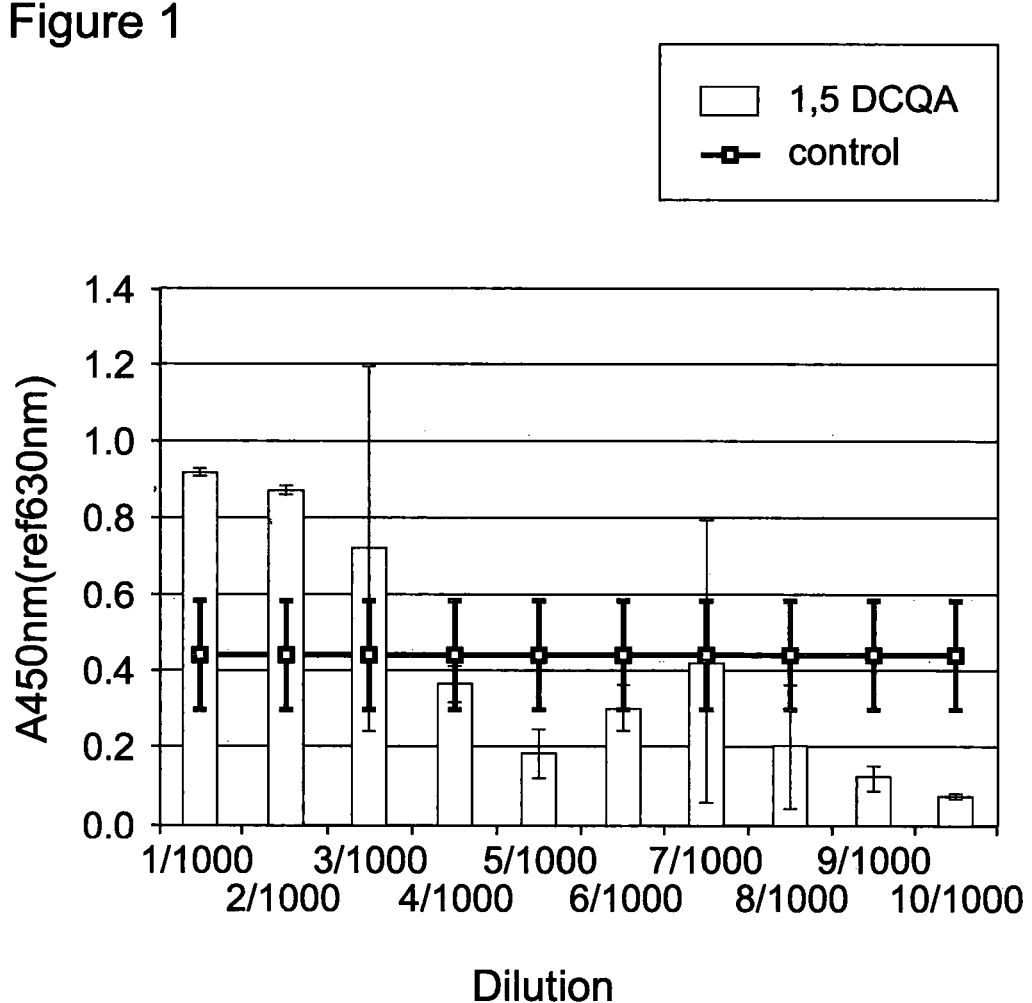
FIG. 1 shows the results of a WST-1 cell proliferation assay of 1,5-Dicaffeoylquinic acid (1,5-DCQA)

With reference to the Figures, there is provided use of a cosmetic composition for the prevention of cell or tissue senescence, the composition comprising a conjugate of quinic acid with at least one molecule of caffeic acid, or a derivative, isomer or salt thereof.

The cosmetic composition comprises a dicaffeoylquinic acid and/or a tricaffeoylquinic acid, or a derivative, isomer or salt thereof. The cosmetic composition comprises a conjugate selected from 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, 3,4,5-tricaffeoylquinic acid, or a derivative, isomer, extract or salt thereof.

Preferably, the conjugate comprises an amino acid, peptide, protein, lipid, sugar, polysaccharide, inorganic or organic acid attached to one of the hydroxyl groups. The conjugate typically comprises an alkyl group or alkaline metal attached at position $R^1$, $R^2$, $R^3$ or $R^4$. Preferably, the aryl or alkyl group or alkaline metal may be attached at position $R^1$.

The composition typically comprises one or more anti-inflammatory agents which may be selected from Boswellia serrata, corosolic acid, ursolic acid, oleanolic acid, salicinol (salacia), rosmarinic acid, ruscogenins, darutoside, asiaticoside, sericoside, harpagoside, horse chestnut (escin, esculin), ginger (gingerol), turmeric extract (tetrahydrocurcuminoids), corydalis, myricetin, artichoke, alfalfa, tea, coffee and/or combinations thereof. The composition may further comprise an anti-inflammatory compound, an antioxidant, an inhibitor of NF-kappaB, an inhibitor of a matrix metalloproteinase, an antibiotic and/or may be administered in combination with an adjuvant treatment. The composition may comprise one or more vitamins, for example, vitamin D, vitamin D3, vitamin C and/or dehydroascorbate, vitamin B, vitamin E, or vitamins or co-factors. The composition may comprise a divalent or polyvalent metal ion or combinations of these selected from copper, zinc, iron, selenium, vanadium and manganese.

The conjugate is preferably a plant extract, and typically an artichoke extract.

The cosmetic composition is typically carried within a vesicle, micelle, liposome, nanoparticle or other suitable vehicle. Typically, the cosmetic composition is applied to the skin. The cosmetic composition may also be applied to the hair and/or scalp. Typically, the cosmetic composition is provided in the form of a serum, lotion, cream, gel, powder, ointment or other medium suitable for the topical administration of the composition to the skin, hair and/or scalp.

Preferably, the cosmetic composition comprises a delivery system comprising skin cleansers, surfactants, skin conditioning agents, hair conditioning agents, vitamins, hormones, minerals, plant extracts, anti-inflammatory agents, anti-oxidants, concentrates of plant extracts, emollients, moisturisers, skin protectants, skin penetration enhancers, solublizers, and/or pH adjusters.

The cosmetic composition is used in the prevention, amelioration and/or treatment of a range of conditions, disorders or diseases which involve the process of senescence. In the context of the present invention, the process of senescence may be natural, premature, induced or accelerated. Accelerated senescence is typically due to genetic or external factors, including but not limited to, chemicals or radiation, including therapeutic radiation. Natural, premature and accelerated senescence are features affecting the skin and its integuments, including hair follicles, and the associated hair growth cycle and natural hair pigmentation. Altered skin texture, thickness and changes in appearance of the skin due to lines and wrinkling are all manifestations of senescence and accelerated senescence, the latter often due to exposure to ultraviolet radiation, and/or smoking.

Advantageously, the cosmetic composition inhibits MMP-9. It is known that MMP-9 is a collagenase and increases the degradation of elastin, gelatine types I and V, collagen type IV and V and fibrillin. Collagen type IV is a major component of the dermal-epidermal junction and Collagen type V is also known to be present in the skin. Breakdown of these components would have a significant role in the reduction of skin firmness. Fibrillin is essential for the formation of elastic fibres in the skin and degradation would reduce the elasticity of the skin. Thus, inhibition of MMP-9 would reduce or prevent the breakdown of these components and thus help to maintain or improve skin elasticity or firmness (Bolognia, Clin Geniatr Med 1993 (9): 209-229; Skjøt-Arkil et al, BMC Pulmonary Medicine 2012 (12): 34; Ashworth et al, Biochem Journal 1999 (340, Part 1): 171-181).

An increased MMP-9 activity is known to cause the breakdown or disturbance of the architecture of the extracellular matrix of the skin and/or may result in UV-irradiation-like damage, which may be exemplified by wrinkling, loss of elasticity and/or dilation of micro-capillary vessels.

Advantageously, the cosmetic composition enhances extracellular matrix cohesion of the skin. Advantageously, the cosmetic composition stimulates the biosynthesis of fibrillar collagens, elastin and/or fibrillins. Advantageously, the cosmetic composition reduces elastin degradation.

Advantageously, use of the cosmetic composition is to improve skin elasticity and/or skin firmness.

Use of the cosmetic composition advantageously protects the skin against environmental damage and/or damage caused by ultraviolet radiation. The cosmetic composition advantageously improves the natural protective functions of the skin, and provides protection against damage that may be caused by pollution, smoking or stress. Advantageously, use of the cosmetic composition improves and/or enhances the appearance of the skin.

Use of the cosmetic composition prevents or ameliorates conditions associated with senescence of the skin, for example, reducing the formation of wrinkles, reducing skin redness, reducing the appearance of telangiectases, delaying the appearance of fine lines, reducing the appearance of dark circles round the eyes, reducing the appearance of blemishes and/or reducing the thinning of the skin.

In another embodiment, use of the cosmetic composition prevents or ameliorates conditions associated with senescence of the hair, for example, reducing loss of hair colour and improving the condition of the hair. Greying of the hair can be a sign of senescence of hair follicles. Although there are many products on the market for using dyes to conceal greying hair, most people would prefer to reverse or slow the natural process of colour change.

With reference to the figures, there is also provided use of a composition for the prevention, amelioration and/or treatment of disorders and diseases involving cell, tissue or organ senescence, the composition comprising a conjugate of quinic acid with at least one molecule of caffeic acid, or a derivative, isomer, extract or salt thereof.

The conjugate may be provided be in the form of a free base, or in the form of a pharmaceutically acceptable salt.

The conjugate may be administered via a pharmaceutically acceptable delivery system which may be in the form of water and oil emulsions, suspensions, colloids, microemulsions, suspensions or emulsions of vesicles, micelles, liposomes or nanoparticles, powders or anhydrous compositions. The conjugate may also be coated or combined with a material such as a lipid, a sugar, or combination thereof. The conjugate may be attached to an amino acid, peptide, antibody or other molecule to enable targeting of the active material to particular cells, tissues or organs. The coating or target-guiding material preferably dissolves to allow efficient and sufficient delivery of the conjugate to cells, tissues or organs.

The composition may be administered by mouth or by a parenteral route. The composition may also be administered via a dermal, intradermal, transdermal, topical, intramuscular, subcutaneous, intravenous, nasal, oral, sublingual, lingual, or rectal route, or by inhalation or instillation. The composition may also be administered by incorporation in an implant or by use of any pumping device. In one embodiment, the composition may be administered in an infusion which is circulated through organs, or added to cells, tissues or isolated organs. The composition may be administered in the form of a tablet.

Advantageously, the composition inhibits p16 INK 4a, and/or modulates MMP-9, NF-kappaB and/or key pro-inflammatory cytokines.

The composition may be used in the prevention, amelioration and/or treatment of a skin disorder or disease.

The composition may be used in the prevention, amelioration and/or treatment of conditions involving senescence of hair follicles, as evidenced by hair loss, thinning of hair and alopecia (which can also be a product of radiation damage). The composition may be used for the prevention, amelioration and/or and treatment of diseases of the hair follicles which are due to a deficiency of the immune system, as in for example alopecia areata and totalis. The composition may be applied to the hair or scalp in the form of a spray, cream, lotion or serum.

The use of the compositions of the invention may also improve the viability and slow the senescence process of stem cells, whether these are obtained from a laboratory process for experimentation purposes, designed for a manufacturing purpose, or a medical purpose. The stem cells may also be artificially produced, cloned or harvested from within the body of a mammal, for example from the tissue of the nose, hair follicle, blood or placenta.

Accelerated senescence has been found to be a feature of certain types of kidney disease in cells, tissues and organs; and may be observed in organs to be used for transplantation purposes, or in cells, tissues or organs which have already been transplanted.

The most important cause of failure of kidney transplants is rejection (Paul L C: Kidney Int 1995, 47; 1491-, Joosten S A et al; Amer J Pathol, 2003, 162(4): 1305-1312), which can occur over a variable period of time. Inspection of the histology of rejected organs demonstrates that there are changes in these organs that are similar to those in the kidneys from older individuals (Melk A et al Am Soc Nephrol 2000, 11: 444-453). It is therefore reasonable to postulate that an increased rate in the process of senescence may be involved in transplanted kidneys and indeed may contribute to deterioration in function and eventual rejection of the graft (Melk A, Halloran P F: J Am Soc Nephrol 2001,12: 385-393). It has also been shown that cells involved in these processes, known as "senescent" cells, contribute to a persistent inflammatory process (Serrano M, Blasco M A: Curr Opin Cell Biol 2001, 13: 748-753). Senescent cells display various changes, including those of shape, shortening of telomeres, collagen and matrix metalloproteinase expression (Dai C Y, Enders G H: Oncogene 2000, 19: 1613-1622 and Linskens M H et al. Nucleic Acids Res 1995, 23: 3244-3251). It is also evident that older kidneys have shortened telomeres (Melk A et al Am Soc Nephrol 2000, 11: 444-453) and that such organs have poorer survival rates of grafts (De Fijter J W J Am Soc Nephrol 2001, 12: 1538-1546).

Further, there is evidence that p16 INK4a accumulates in these cells and is concerned in the maintenance of senescence (Sherr C J, Roberts J M: Genes Dev 1999, 13: 1501-1512 and Stein G H et al Mol Cell Biol 1999, 19: 2109-2117). An increase in expression of senescence associated cell-cycle inhibitor p16 INK4a has been found both in deteriorating kidney transplants and in diseased kidneys (Melk et al, American Journal of Transplantation, 2005, 5(6): 1375-82). It has also been demonstrated that the expression lasts during the chronic rejection phase.

Control of the expression of p16 INK4a throughout the whole process of chronic graft rejection could therefore be of prime importance in increasing the prospects of graft survival. The therapeutic control of p16 INK4a expression and oxidant damage may also be very important in older organs and tissues which could be made available for transplantation, thus increasing the numbers of organs and tissues which could be used. There is also evidence that in autologous hair transplantation, a variable percentage of transplanted plugs are rejected. Although the mechanism of this process is not known, a similar one to that described above may be involved.

Diseased organs demonstrate signs of cellular senescence and therefore should benefit from the therapeutic control of p16 INK4a and oxidant damage. Since the compositions preferably have potent anti-senescent and anti-oxidant properties, they may be candidates not only for use as a therapeutic to counter the senescent process in older cells, tissues and organs in health and disease, but also for use in transplanted cells, tissues and organs where the senescence process is a cardinal feature of rejection. It is also to be noted that since the compositions may be used to ameliorate accelerated senescence in skin, they could also be used for the purposes of counteracting this process.

The composition may be used in the prevention, amelioration and/or treatment of conditions associated with neurodegeneration.

The blood brain barrier exists to keep unwanted substances from the blood entering brain tissue, but allows essential materials to gain access through specialised transporters. These are essentially the properties of the cerebral endothelial cells which control both the permeability of the junctions between them and the ingress, via complex ports, of substances such as glucose, amino acids, vitamins, certain hormones, etc. These cells also express a number of specialised enzymes on their surfaces, indicating that the blood brain barrier is highly complicated and tightly controlled in normal health. Permeability of the blood brain barrier is also supported by factors emanating from cells on the abluminal side of the endothelial cells. Cells such as astrocytes can be regarded as very important to the blood brain barrier since they make physical contact with over 90% of the single layered endothelium. Other cells within the brain tissue, including glial cells and pericytes, are also very important to the normal functioning of the blood brain barrier. An increase in permeability of the blood brain barrier can occur from loss of integrity of the normally highly restrictive tight and adherens junctions. In certain diseases and conditions affecting the central nervous system there is evidence of greater permeability of the blood brain barrier. This occurs in the neurodegenerative diseases such as Multiple Sclerosis, Parkinson's disease and Alzheimer's disease, but also in stroke where there can be considerable disruption in those parts of the blood brain barrier close to the site of the lesion. Abnormal permeability is also observed in sepsis and the attendant inflammatory processes.

Since there is evidence that IL-6 and MMP-9 play significant roles in increasing blood brain barrier permeability, the composition, which may inhibit both IL-6 and MMP-9, may provide a therapeutic approach in regaining control of the permeability and healing of the blood brain barrier. In this way, the composition may help ameliorate the relapsing phase of Multiple Sclerosis, and may be used to slow or stop the ingress of unwanted and therefore deleterious substances in Alzheimer's disease, stroke and inflammatory conditions of the central and peripheral nervous systems.

Alzheimer's disease is the commonest cause of dementia, afflicting some 26 to 30 million people worldwide. There is no known cure and treatment is based on relieving symptoms. The cause of this disease is not known but primarily, it is understood to be related to increasing age. However, genetic components play an important role in conditions such as Down's Syndrome, whose sufferers are prone to developing Alzheimer's disease as more live into older age. Classical pathological studies reveal widespread loss of mainly cortical neurones, the presence of amyloid plaques and neurofibrillary tangles (Donev et al. J Cell Mol Med 2009; 13: 4329-4348). Several hypotheses have been put forward to explain the cause of Alzheimer's disease. The two main hypotheses are: (a) that beta-amyloid deposits (plaques) are the causative agents; or (b) that changes occur in the tau protein with hyperphosphorylation resulting in tangles and disintegration of the cell transport system (microtubules). Recently, it has been shown that peptide fragment 1-42 from beta-amyloid is capable of causing neurotoxicity. So far, no mechanism has been advanced to explain the main features of Alzheimer's disease which would allow a rational approach to the treatment of this disease.

It has been demonstrated that SIRT2 is able to activate gamma secretase which cleaves the transmembrane domain of amyloid precursor protein (APP) thus releasing amyloid-beta and encouraging plaque formation. SIRT2 suppresses alpha-tubulin, a key protein in the structures of microtubules, the major cell transport system (North et al, Mol Cell, 2003: 11(2) 437-444). This leads to dysfunction of microtubules, disintegration and tangle formation. Thus, SIRT2 can activate gamma secretase and, in turn, presenilin-dependent gamma-secretase activity affects neurite outgrowth (Figueroa et al, Neurobiology of Disease, 2002; vol 9, 49-60). This may contribute to the neuritis, which is characteristic of the pathology of Alzheimer's disease. It has been shown in models of Parkinson's disease that inhibition of SIRT2 may rescue alpha-synuclein mediated toxicity (Outieri, Science, 2007: vol 317 516-519). SIRT2 may also have this property in Alzheimer's disease. Suppression of the over expression of SIRT2 may therefore play an important role in the treatment of Alzheimer's disease.

Advantageously, the suppression of SIRT2 by use of the composition may encourage neurite outgrowth from cortical neurones, inhibit the cleavage of amyloid-beta from APP and hence slow the formation of amyloid plaques. Through relieving the suppression of alpha-tubulin, the composition may help maintain the integrity of microtubules. The integrity of the mitochondria is very important to the functioning of the cell since the loss of these bodies will hasten cell senescence and apoptosis. Therefore, the up regulation of sirtuin 3 (SIRT3) may help maintain the integrity of mitochondria in Alzheimer's disease by suppressing mitochondrial reactive species (Kong et al, PloS One, 2010: 5(7): e11707). Additionally, SIRT3 also cleaves APP at a locus which provides a fragment of APP. However, in contrast to SIRT2 cleavage, the cleavage by SIRT3 produces a fragment that is not amyloidogenic. This is important in the treatment of Alzheimer's disease. The use of the composition to up regulate SIRT3 and down regulate SIRT2 decreases the amyloidogenic fragment and increases the non-amyloidogenic fragment of APP, therefore offering a rational approach to the treatment of Alzheimer's disease.

Advantageously, the composition may be used in the prevention, amelioration and/or treatment of Parkinson's disease. MMP-9, which may be inhibited by the composition, has been shown to be neurotoxic to the dopaminergic neurones of the substantia nigra (Lorenzl et al, Neuromolecular Med, 2004; 5(2): 119-132) and to be able to cleave terminal sequences from alpha-synuclein, thereby creating toxic aggregates of the latter which are present in Lewy bodies (an important pathological sign of this disease), and neuronal destruction. In addition, MMP-9 is involved in processes leading to increased permeability of the blood brain barrier, allowing unwanted molecules to penetrate brain tissue. IL-6 is also known to up regulate MMP-9, thus amplifying the effect on the blood brain barrier. Thus, the inhibition of MMP-9 and IL-6 is very important in the treatment of this condition. MMP-9 is up regulated by CXCL8 (IL-8) and by NF-kappaB. The latter also up regulates interleukin-1, which in turn can stimulate microglia to produce key cytokines. Analysis of the known principal molecular pathways associated with the pathology of Parkinson's disease suggests that the enzyme MMP-9 may play an important role in the development of the process leading to the now well recognised histological, biomolecular, and clinical features of this disease. There is increasing evidence that the pathology of Parkinson's disease involves an inflammatory process and greater levels of pro-inflammatory cytokines have been found in the brains of patients who have suffered from this condition. Further, in this disease, a relationship has been found between plasma NF-kappaB, p65 levels and certain cytokines.

Sirtuin 2 has been shown to enhance toxin induced nigro-striatal damage by deacteylating Forkhead box 03a (FOXO3a) (Lin et al, J. Biol. Chem., 2012; 287: 32307-32311). Additionally, SIRT2, a cell senescence-based deacetylase, may be closely associated with the protein alpha-synuclein since inhibition of SIRT2 by pharmacological means protects neurons and may rescue the toxicity produced by alpha-synuclein in cell systems (Outieri, Science, 2007: vol 317 516-519). In the CNS, SIRT2 is an oligodendroglial protein also involved in the control of differentiation. This sirtuin has an inhibitory action on alpha-tubulin, a key component of the microtubular architecture and, if present in excess, can be detrimental to the integrity of the cell. Therefore, SIRT2 itself can be regarded as a possible therapeutic target for neurodegenerative disease including Parkinson's disease.

Multiple Sclerosis is a chronic disease of the central nervous system which involves progressive destruction of myelin. In many patients the associated axons are also damaged or destroyed. In addition, the blood brain barrier may also be rendered more permeable to unwanted molecules and cells of the blood. The aetiogy of Multiple Sclerosis is unknown at present, but it is likely that there are many factors contributing to this complex disease. Cytotoxic pro-inflammatory cytokines, proteases, including MMPs, and reactive oxygen species all may, in part, contribute to the destruction of myelin. The breakdown of tight junctions has been noted in active Multiple Sclerosis and may involve the down regulation of the gene expression of junction proteins in endothelial cells. It is thought that pro-inflammatory cytokines such as tumour necrosis factor-alpha (TNF-alpha), interleukin-6 (IL-6) and interferon-gamma (IFN-gamma) may be involved. Studies also indicate that the chemokine CXCL8 (IL-8) may also be increased. MMP-9 has also to be found up regulated in Multiple Sclerosis patients although normally absent in cerebrospinal fluid (CSF). Over expression of MMP-9 is therefore regarded as of considerable importance in the pathology of Multiple Sclerosis, in addition to increasing the permeability of the blood brain barrier.

Thus cytotoxic pro-inflammatory cytokines TNF-alpha, IFN-gamma and IL-6 (which are all up regulated by NF-kappaB), the chemokine CXCL-8 (IL-8) and MMP-9 are all potential targets in the rational approach to the therapy of Multiple Sclerosis.

In the CNS, SIRT2 is also an oligodendroglial protein involved in the control of differentiation. It has an inhibitory action on alpha-tubulin, a key component of microtubular architecture and, if present in excess, can be detrimental to the integrity of the cell. Therefore, SIRT2 is also a potential therapeutic target for Multiple Sclerosis. The composition may advantageously inhibit NF-kappaB and MMP-9, inhibit SIRT2 activity and up-regulate SIRT3 which protects against apoptosis. Inhibition of SIRT2 has also been shown to rescue the toxicity of alpha-synuclein, a neurotoxic protein which produces neuronal apoptosis (Outieri, Science, 2007: vol 317 516-519). As a result of these findings, the composition may therefore be used in the treatment of Multiple Sclerosis. In addition, Interferon-gamma (IFN-gamma, which is also inhibited by the use of the composition) phosphorylates Eph 4a. Phosphorylated Eph 4a inhibits the function of neurons, astrocytes and glia. Since astrocyte function is diminished, leukaemia inhibition factor (LIF) secretion from these cells is diminished. Since LIF is required to stimulate oligodendrocytes to produce myelin, remyelination of axons is also diminished. Indirectly therefore, both SIRT2 and interferon-gamma adversely affect the remyelination process. Interferon-gamma which induces demyelination of myelinated axons therefore also indirectly inhibits remyelination. These phenomena are hallmarks of Multiple Sclerosis. The inhibition of SIRT2 and also of IFN-gamma by the composition may therefore provide a possible therapy for Multiple Sclerosis. Since SIRT2 adversely affects neurons associated with Parkinson's disease, Alzheimer's disease and Multiple Sclerosis collectively, it may be a common feature influencing the development of neurodegeneration.

The composition may be used in the prevention, amelioration and/or treatment of mitochondriopathies, including the neuromitochondriopathies. Advantageously, the composition may contribute to repair of mitochondrial DNA by up regulating sirtuin 3 and thus encouraging the interaction of sirtuin 3 with 8-oxoguanine-DNA glycosylase (OGG1), a DNA repair enzyme (Cheng et al, Cell Death Dis, 2013, 4e731).

In addition to the above, the composition may be used in reversing senescence-associated degeneration of cells, including stem cells, and those of the central and peripheral nervous systems. Underpinning these properties is the observation that these compounds increase the cellular levels of sirtuin 3 (SIRT3) and decrease the level of sirtuin 2 (SIRT2). These proteins are known to regulate the processes governing cell senescence, wherein SIRT3 is associated with decreasing and SIRT2 is associated with increasing senescence. The well-known biomarker of cell senescence p16 may also be inhibited by the use of the composition (see FIG. 2).

The safety of the composition when applied to human cells is evidenced by its effect on the XRCC 5 gene (see FIG. 4), even in conditions when this gene was sub-lethally stressed with oxidant. XRCC5 is a double strand break repair gene which was unaffected under stressed conditions, indicating that the composition did not induce double strand breaks in DNA. Human lymphocyte counts after mitogen stimulation with phytoagglutinin (PHA) did not diminish significantly during experiments, further indicating the safety of the composition.

The use of the composition to inhibit key pro-senescence proteins and genes, including NF-kappaB, pro-inflammatory cytokines, p16 INK4a and sirtuin 2, together with the up regulation of sirtuin 3 may therefore offer prevention, amelioration and/or treatment of a range of conditions and diseases in which these are over expressed, including those of the skin and other tissues and organs. The up regulation of sirtuin 3 by the use of the composition may not only provide a positive drive against the senescence process, but may be able to reverse some of the cellular changes induced by the senescence process.

With reference to the figures, there is also provided use of a composition as defined in the first aspect for the prevention, amelioration and/or treatment of disorders and diseases involving cell, tissue or organ stress caused by an inflammatory process, the composition comprising a conjugate of quinic acid with at least one molecule of caffeic acid, or a derivative, isomer, extract or salt thereof.

The composition may be used for the prevention, amelioration and/or treatment of disorders or diseases associated with an increase in the expression of MMP genes and/or proteins. In a preferred embodiment, the composition inhibits MMPs, NF-kappa B, and/or tissue inhibitors of matrix metalloproteinase (TIMP) activators. In one embodiment, the disorder or disease is associated with an increase in the expression of MMP-9 and/or MMP-2. Typically, the composition inhibits MMP-9 and/or MMP-2. MMP-9 has been found to be present at increased concentrations in the cells, tissues, organs or plasma in certain conditions and diseases.

The composition may be used for the prevention, amelioration and/or treatment of conditions and diseases in which MMP-9 is over expressed.

Advantageously, the composition may be used for the prevention, amelioration and/or treatment of disease in which the inflammatory process is in part, either in acute or chronic form. In diseases in which there is an acute inflammatory reaction, particularly those caused by infective organisms, the concentration of MMP-9 has been found to be increased in the plasma, and is often present in high concentrations. In diseases where there are signs of an inflammatory reaction, there is evidence that MMP-9 concentrations in tissue, organs and/or plasma are raised above constitutive levels. The inflammatory process manifested in many diseases and disorders may be acute or chronic due to the presence of infective organisms, for example, bacteria, viruses, and parasites, or may be an integral part of an underlying disease. Some examples of diseases and disorders in which inflammation plays a role and in which MMP-9 is over expressed include: conditions due to a infective organism (for example, bacteria, viruses or parasites); osteoarthritis; rheumatoid arthritis; gout; Sjögren's syndrome; synovitis; injuries to tendon, muscle, cartilage and bone; laminal inflammation in horses; auto-immune disorders, including lupus erythematosis; Kawasaki disease; skin ulceration; burns; urticaria; periodontitis; bronchiectasis; bronchiolitis; chronic obstructive pulmonary disease; emphysema; atopic dermatitis; psoriasis; stored blood inflammation; aneurysms; gastric and colon ulceration; Crohn's disease; colitis; pelvic inflammatory disease; appendicitis; pancreatitis; degenerative diseases of the central nervous system including generalised and focal cerebral ischaemia; encephalitis; ophthalmopathy; uveitis; open-angle, ocular surface disease; myocardial ischaemia; infarction and fibrosis; coronary heart disease; heart failure; atheromatous plaque instability; aneurysms and the inflammatory response observed in certain genetic disorders including Huntington's disease and motor neurone disease.

The use of the composition advantageously inhibits key pro-inflammatory proteins such as TNF-alpha and MMP-9, and may be used in the amelioration and/or treatment of diseases and disorders involving over expression of MMPs, such as chronic inflammatory disorders and conditions where an inflammatory process is prevalent, or in neoplastic progression and metastases.

The composition may be used for the prevention, amelioration and/or treatment of a malignant or benign neoplasm. Preferably, the malignant neoplasm may be associated with breast, lung colon, rectum, prostate, blood cells, oral cancer, skin cancer or melanoma, and/or leukaemia.

In a further embodiment, the composition may be used method for the prevention, and/or treatment of cancer and cancer metastasis. An increased concentration of MMP-9 has been found in many cancers, for example in prostate and breast cancer, and in melanoma. As mentioned previously, MMP-9 is involved in the invasion of surrounding tissues by disordering the extracellular matrix, and is also involved in the spread of cancer cells to lymphatic glands, distant tissues and organs. A large number of cancers have been shown to over express MMP-9 in the primary, invasive and metastatic phases of the disease. Most of the studies carried out have been on breast cancer, prostate cancer, colon cancer and melanoma. Other examples of cancers in which MMP-9 is over expressed include leukaemia, multiple myeloma, lung cancer, mesothelioma, hypopharyngeal and salivary gland cancers, oesophageal cancer, gastric cancer, renal cancer, bladder cancer, ovarian cancer, endometrial cancer, basal and squamous cell cancers of skin.

The composition may be used for the treatment of cancer in combination with one or more anti-cancer drugs and/or treatment, including the use of radiotherapeutic, ultrasonic, phototherapeutic, chemotherapy, radiotherapy and/or surgery.

It has been demonstrated that MMP-9 is involved in the extension of a primary malignant neoplasm and in metastasis. Whilst the composition is not an anti-mitotic drug per se, it may be used to inhibit MMP-9 secreted by the primary neoplasm, the metastases, and surrounding cells, hence slowing or preventing further extension.

In the neoplastic process, MMP-9 may be up regulated, thus causing disruption of the extracellular architecture and creating a milieu for cancer cell proliferation in the primary tumour locus and in metastatic disease.

Cancer is one of the major causes of death in industrial countries and most deaths are from metastases which are refractory to treatment. Most cancers therefore cannot be treated optimally at present. Apart from the intrinsic properties of the cancer cell to grow continuously, the development and progression of the primary tumour depends on the microenvironment of the malignant cells which surprisingly may exhibit all the features of inflammation. It has been demonstrated that one of the main drivers of the inflammatory process is NF-kappaB which can indirectly affect the architecture of the extracellular matrix via MMP-9, allowing the primary tumour cell mass to expand further into this area. A continuing inflammatory process may therefore ensure further tumour expansion. Controlling the inflammation surrounding the tumour mass may assist in containment of the tumour and in reducing metastasis. Thus, use of the composition may assist in tumour containment due to inhibition of NF-kappaB and MMP-9. The composition may be administered in combination with an anti-mitotic drug to offer a rational approach to treatment, which may advantageously have a lower level of toxicity for the patient. The composition may also be used to reduce the metastatic spread of a tumour to the lymph nodes, distant tissues and organs. In normal conditions, NF-kappaB is kept constrained in the cytoplasm of the cell by being linked to IKB kinase (IKK) in the signaling module IKK/NF-kappaB. NF-kappaB is activated by release from the module and is translocated from the cytoplasm to the nucleus of the cell, where it binds at relevant sites. NF-kappaB effects the transcription of genes encoding a number of important proteins in this process, including pro-inflammatory cytokines such as interleukin-1 (IL-1), interleukin-6 (IL-6), tumour necrosis factor-alpha (TNF-alpha) and interferon-gamma (IFN-gamma). The MMPs, angiogenic and growth factors are also up regulated in this process. NF-kappaB therefore mediates the process of cell proliferation, tumour promotion and the inflammatory process, together with the lymphatic and distant spread of cancer. This transcription factor is also linked to resistance to anti-mitotic therapy, both by drugs and radiation. Thus, NF-kappaB is a very important target for drugs in the treatment approach of cancer. The composition inhibits NF-kappaB by preventing the phosphorylation of serine 536 of the p65 subunit of NF-kappaB, thus preventing this transcription factor from binding to the relevant DNA site. Advantageously, the composition inhibits MMP-9, the pro-inflammatory cytokines TNF-alpha, IL-1 beta, IL-6 and IFN-gamma.

The use of the composition advantageously reduces the inflammatory component in muscular dystrophies, other muscle diseases and injuries, tendon, synovial and cartilage tissues.

The composition may be used for the amelioration and/or treatment of muscular dystrophy which comprises a set of closely related genetic disorders including Duchenne muscular dystrophy, where there is an absence of the protein dystrophin, and the lower girdle muscular dystrophy (LGMD), where there is an absence of the protein fukutin-related protein (FKRP). In these conditions, inflammation of the muscles occurs due to the ingress of monocytes (macrophages) which secrete MMP-9, resulting in an increased damage to the extracellular matrix of muscle thereby attracting more extrinsic monocytes. This causes more inflammatory damage which leads to increasing fibrosis of affected muscle and increasing physical disability. The effective inhibition of MMP-9 may break this cycle, ameliorate the damage to muscle and help slow the progression of this disease.

Duchenne muscular dystrophy is an X chromosome-linked recessive genetic disorder affecting approximately 1 in 3500 live male births. Children with this disorder typically show early signs of muscle degeneration which may progress to an inability to walk, usually occurring before puberty. Patients with this condition typically die from respiratory and heart dysfunction by the age of 30 years. The dystrophin protein is essential for the structural integrity of muscle and its normal functioning and is part of a complex of proteins which link the extracellular matrix (ECM) to the mechanical cytoskeleton of muscle. Thus, this protein is involved in the provision of mechanical stability and is part of the signalling system linking the ECM to the contractile elements. Mutations in the dystrophin gene lead to an absence of dystrophin protein in the protein chain complex, resulting in the clinical picture which was originally described by Duchenne. These disturbances in mechanical signalling result in further changes in the affected muscles, which may include severe damage to the muscle membrane which may allow ingress of various cells of the immune system, particularly of macrophages. This may lead to a chronic inflammatory process, fibrosis and eventual degeneration of muscles.

There are two pathological factors involved in Duchenne muscular dystrophy: first, the dystrophin gene mutation; and second, an ongoing inflammatory process resulting in an impaired or absent muscle regeneration. Both of these factors contribute to the progression of the disease. It has been demonstrated that the concentration of the pro-inflammatory cytokine tumour necrosis factor-alpha (TNF-alpha) is up regulated in the muscles of both animal models and those of Duchenne muscular dystrophy patients, mainly due to the ingress of inflammatory cells. TNF-alpha is a powerful activator of NF-kappaB, the transcription factor which is intimately involved in the inflammatory response. Persistent and chronic activation of NF-kappaB can produce pathological changes in many different cell types, tissues and organs, as observed in diverse clinical diseases, and has been shown to be present in various conditions and diseases of skeletal muscle including muscle atrophy, Duchenne muscular dystrophy and limb-girdle muscular dystrophy (LGMD). The signalling complex IKK-NF-kappaB has been shown to be important in muscular dystrophy and is therefore a legitimate target for possible pharmacological intervention. Furthermore, there are two components of this signalling process, one originating from damaged skeletal muscle and the other from the immune cells which infiltrate the damaged muscle. The signalling process involves downstream MMP-9 which, due to the involvement in the inflammatory process, is also a therapeutic target. The composition is capable of inhibiting NF-kappa B, MMP-9 and pro-inflammatory cytokines, in addition to the pro-apoptotic p16 gene, and may therefore be used in the amelioration and/or treatment of Duchenne muscular dystrophy.

Over expression of NF-kappaB and MMP-9, with the associated downstream consequences, are also present in other muscular dystrophies, such as lower-girdle muscular dystrophy (LGMD-2B), which condition is caused by a mutation in the gene. Although LGMD-2B is different from Duchenne muscular dystrophy due to the absence of a protein (FKRP), and may be of later onset than Duchenne muscular dystrophy, LGMD-2B involves the destruction of muscle fibres and a chronic inflammatory process, which factors are present in Duchenne muscular dystrophy. The composition is capable of modulating the deleterious effects of the over expression of NF-kappa B, MMP-9 and pro-inflammatory cytokines, thus assisting in the prevention, amelioration and/or treatment of LGMD-2B.

Thus, the composition may be used to inhibit MMP and pro-inflammatory proteins, in particular TNF-alpha. The latter is known to activate NF-kappa B which in turn up regulates MMP-9, thereby creating a self-sustaining pro-inflammatory and MMP-9 generating loop. In turn, MMP-9 (an endopeptidase) can excise a terminal amino acid sequence from alpha-synuclein (a protein normally associated with the pre-synaptic region of neurones), giving rise to other forms of this protein, including insoluble compounds which are neurotoxic and found in Lewy body structures in Parkinson's Disease. The activity and hyperactivity of the MMPs may therefore be involved in the degenerative processes in diseases of the nervous system.

The composition may be used in the prevention, amelioration and/or treatment of cells, tissues or organs in inflammatory diseases or disorders, where MMPs are over expressed, for example, in wound healing. The composition may also be used in modulating or controlling the over expression of MMPs in secondarily affected cells, tissues or organs, for example, in conditions associated with an increase in the permeability of the blood brain barrier, or in conditions including stroke.

The composition may be used for the prevention, amelioration and/or treatment of diseases of the musculo-skeletal system in mammals, in which the inflammatory process is part.

The composition may be used for the prevention, amelioration and/or treatment of muscular dystrophies, tendons, synovial membranes, cartilage and muscle injuries. Advantageously, use of the composition may diminish, attenuate or inhibit the output of MMPs, preferably MMP-9, an enzyme which has been found to be present in increased concentrations in the cells, tissues, organs or serum in certain conditions, disorders and diseases.

The composition may be used for the prevention, amelioration and/or treatment of conditions or disorders associated with the bowel in which there is an acute or chronic inflammatory component. An acute inflammatory condition of the bowel may be produced by infection, usually by bacteria or parasites, as for example in *Clostridium difficile* infection; or in the chronic or acute phases of an underlying infective pathology, as for example in Crohn's disease or ulcerative colitis. The composition may also be used in the prevention, amelioration and/or treatment of irritable bowel syndrome.

The composition may be used for the prevention, amelioration and/or treatment of diseases of the eye. MMPs may be involved in acute and chronic diseases of the eye where there is an infective or inflammatory component, or where the MMP may be over expressed as part of a disease process. These diseases may include, but are not limited to, conjunctivitis, blepharitis, dry eye, uveitis, macular degeneration, corneal opacities, glaucoma, diseases of the lens and/or retina.

The composition may be used for the prevention, amelioration and/or treatment of diseases of the respiratory system in which there is an inflammatory component. Elevated levels of MMP-9 have been demonstrated in individuals with bronchiectasis, chronic obstructive pulmonary disease (COPD) and/or in asthma.

The composition may be used for the prevention, amelioration and/or treatment of rheumatoid arthritis and/or osteoarthritis.

The composition may be used for the prevention, amelioration and/or treatment of the fragile X syndrome (FXS) a disorder in which there is an absence of a protein called fragile X mental retardation protein (FMRP), in affected neurons. This condition is due to a mutation in the FMR1 gene, known to be due to the methylation of the regulatory region, effectively silencing the gene. This results in deformities of the dendritic spines of the neurons and subsequent loss of the ability to receive incoming signals from other neurons. Cognitive development is therefore significantly curtailed. It has been shown that the inhibition of MMP-9 in FMR1 gene knockout mice results in maturation of dendritic spines, pointing to a possible role for an MMP-9 inhibitor in the treatment of this disease.

In a further embodiment, the composition may be used for the prevention, amelioration and/or treatment of fatigue, particularly that of chronic fatigue syndrome (myalgic encephalomyelitis) and that following viral infection (post viral fatigue syndrome).

Compositions in accordance with the invention are preferably used in human therapeutics, but may also be used in veterinary practice. In the latter, the applications may be applied to a mammal, whether in the laboratory, in captivity, or in the wild, on a farm, in industry, domestic or sporting situations.

Other objectives, advantages and scope of the composition will be presented in the detailed description and will become understood by those skilled in the art, or learned by practice in its use.

The following results shown in FIGS. 2 to 7 relate to the analysis of Senescence tests on compound 2066 (1,5-dicaffeoylquinic acid or 1,5-DCQA). The experiments were conducted using Human Foreskin Fibroblasts (HFFs).

FIG. 1 shows the results of a WST-1 Cell Proliferation Assay of 1,5-DCQA in HFFs. The WST-1 Cell Proliferation Assay provides a sensitive and accurate assay for cell proliferation and cytotoxicity (cell viability). The WST assay is based on the cleavage of the tetrazolium salt WST-1 to formazan by cellular mitochondrial dehydrogenases. Expansion in the number of viable cells results in an increase in the overall activity of the mitochondrial dehydrogenases in the sample. The augmentation in enzyme activity results in an increase in the amount of formazan dye formed. The formazan dye produced by viable cells was quantified by a multi-well spectrophotometer by measuring the absorbance of the dye solution at 440 nm. The compound provided was tested in the WST assay over a range of dilutions. The data generated indicated that 1,5-Dicaffeoylquinic acid appeared to be beneficial to cell viability at 1/1000 and 2/1000 dilutions. Table 1 and FIG. 1 show the results of the WST-1 Cell Proliferation Assay. The results of the assay show the standard deviation (SD) for 1,5-DCQA (2066) and the control, and the mean values for 1,5-DCQA (2066) and the control.

TABLE 1

| Mean 2066 | Mean Control |
|---|---|
| 0.916 | 0.438 |
| 0.868 | 0.438 |
| 0.717 | 0.438 |
| 0.363 | 0.438 |
| 0.178 | 0.438 |
| 0.300 | 0.438 |
| 0.419 | 0.438 |
| 0.196 | 0.438 |
| 0.115 | 0.438 |
| 0.069 | 0.438 |

| SD 2066 | SD Control |
|---|---|
| 0.007 | 0.140 |
| 0.011 | 0.140 |
| 0.477 | 0.140 |
| 0.047 | 0.140 |
| 0.064 | 0.140 |
| 0.059 | 0.140 |
| 0.370 | 0.140 |
| 0.161 | 0.140 |
| 0.030 | 0.140 |
| 0.005 | 0.140 |

In the following experiments, HFFs were challenged for a period of two hours with 150 µM hydrogen peroxide ($H_2O_2$), to stimulate premature senescence in the presence and absence of 1,5-Dicaffeoylquinic acid (1/1000 dilution), and subsequently assayed by Taqman Real Time-PCR for the expression of key senescence associated genes.

Figure 2:
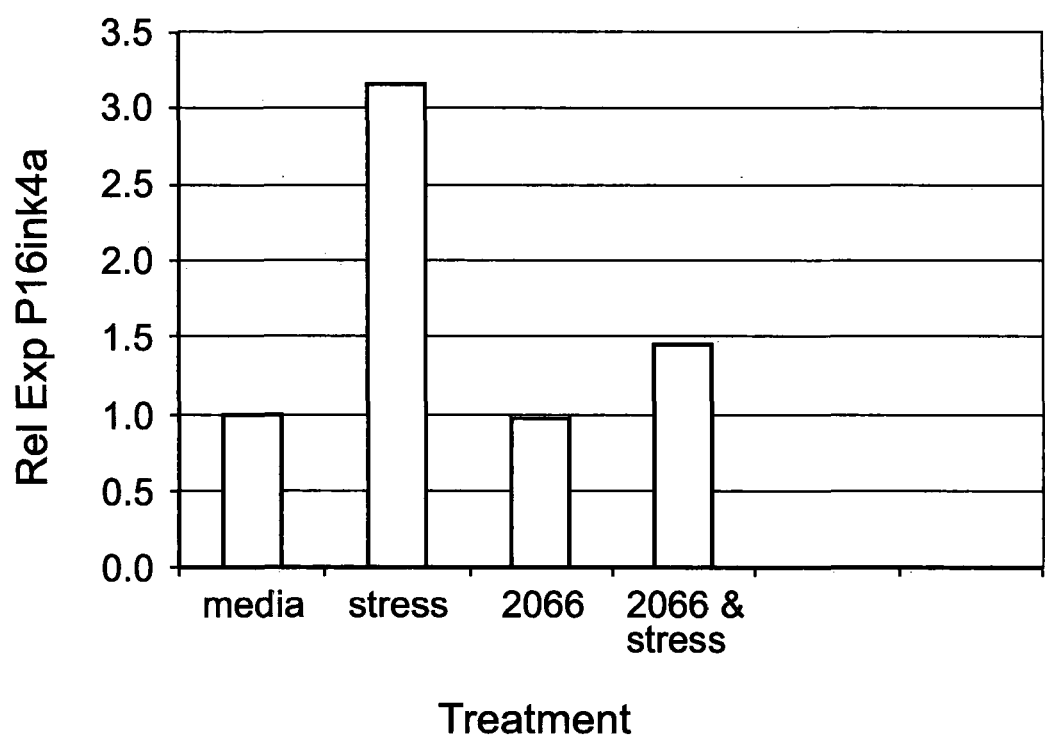
FIG. 2 shows the results of expression of p16 in cells following incubation with 1,5-DCQA.

FIG. 2 shows the relative expression of p16 in HFFs incubated with 1,5-DCQA with and without stress-induced premature senescence with 150 µM $H_2O_2$. The results indicate that 1,5-Dicaffeoylquinic acid had no stress effect on untreated cells (i.e. no $H_2O_2$) and gave excellent protection from oxidant challenge, as no gross increase in expression was observed following insult.

Figure 3:
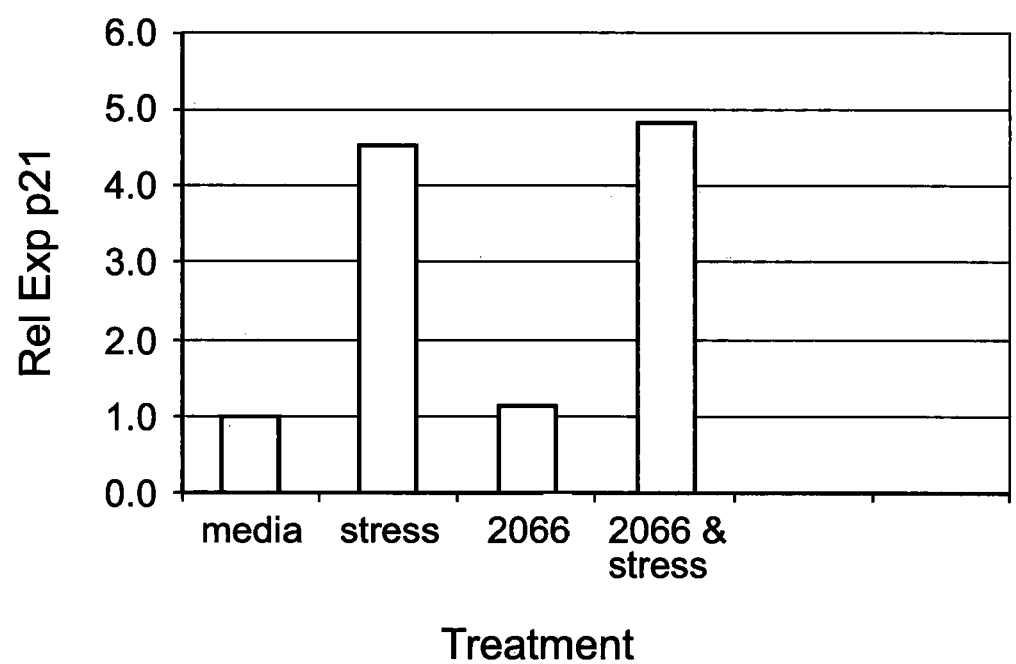
FIG. 3 shows the results of expression of p21 in cells incubated with 1,5-DCQA.

FIG. 3 shows the relative expression of p21 in HFFs incubated with 1,5-DCQA with and without stress-induced premature senescence with 150 µM $H_2O_2$. As the inhibition mediated with 1,5-DCQA is known to occur downstream of the p21 gene, the expression levels are substantially unchanged following stress.

Figure 4:
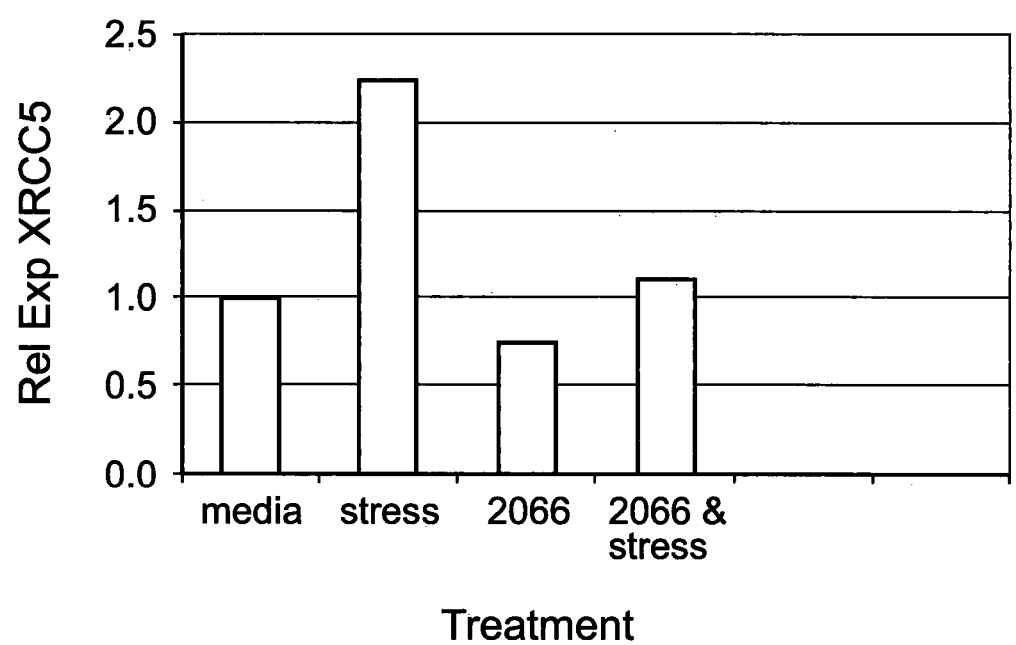
FIG. 4 shows the results of expression of XRCC5 in cells following incubation with 1,5-DCQA.

FIG. 4 shows the relative expression of XRCC5 in HFFs with 1,5-DCQA with and without stress-induced premature senescence with 150 µM $H_2O_2$. XRCC5 is a double strand break repair protein. The substantially unaltered expression of XRCC5, in comparison with the control data set, indicates that the compound does not induce DNA breaks per se and mitigates against the effects of oxidant challenge.

Figure 5:
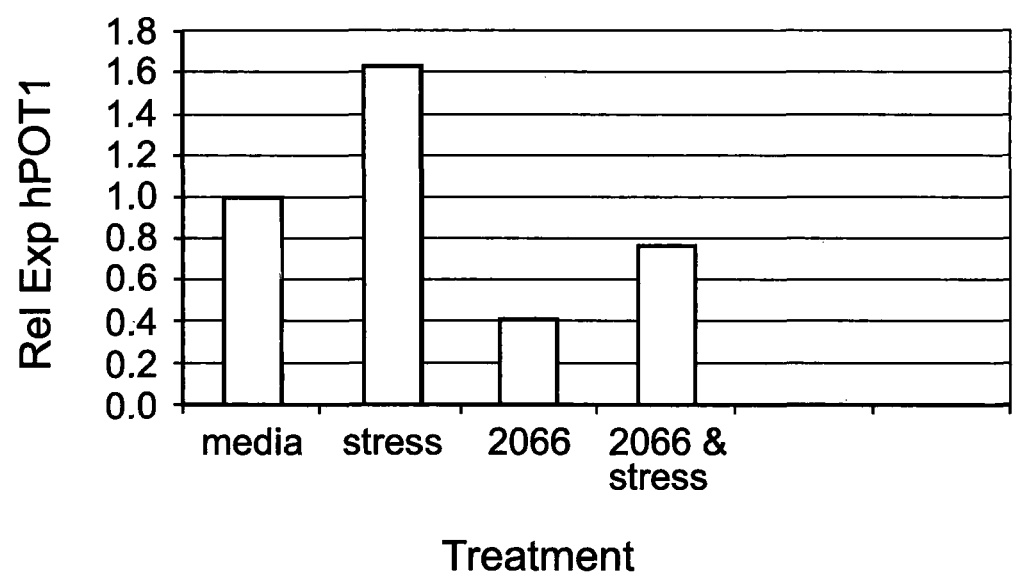
FIG. 5 shows the results of expression of hPOT1 in cells following incubation with 1,5-DCQA.

These findings are supported by an analysis of the Protection of Telomeres gene (POT 1). FIG. 5 shows the reltive expression of hPOT1 in HFFs incubated with 1,5-DCQA with and without stress-induced premature senescence with 150 µM $H_2O_2$. The results indicate a protective effect induced the compound against oxidant challenge, consistent with the previous data sets.

Figure 6:
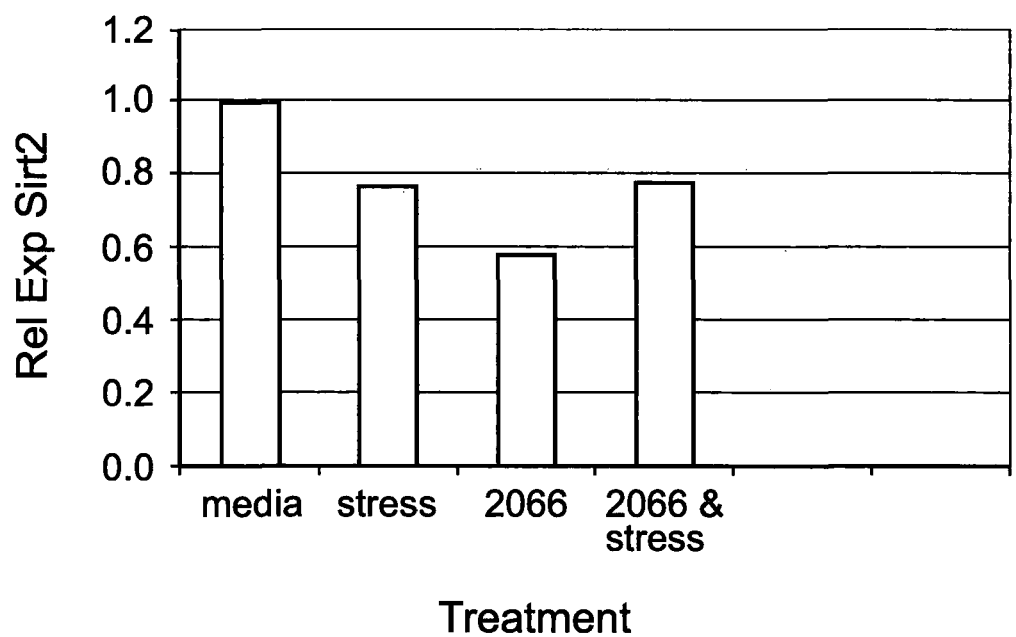
FIG. 6 shows the relative expression levels of sirtuin 2 in cells following incubation with 1,5-DCQA.
Figure 7:
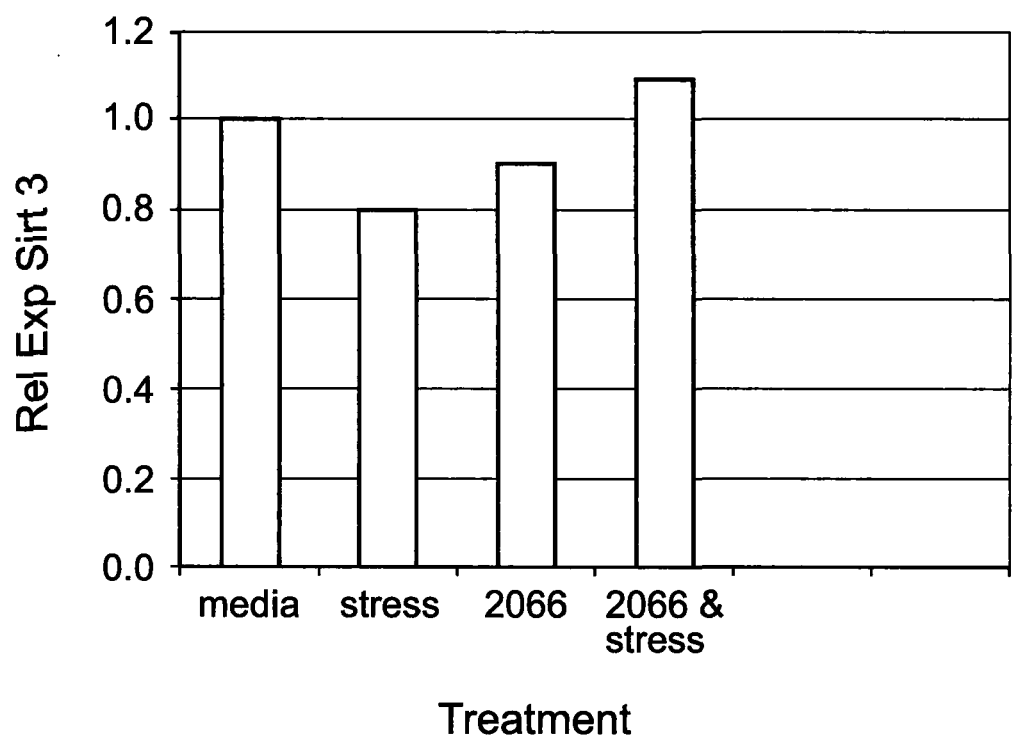
FIG. 7 shows the relative expression levels of sirtuin 3 in cells following incubation with 1,5-DCQA.

FIG. 6 shows the relative expression of Sirtuin 2 (SIRT2) in HFFs incubated with 1,5-DCQA with and without stress-induced premature senescence with 150 µM $H_2O_2$. FIG. 7 shows the relative expression of Sirtuin 3 (SIRT3) in HFFs incubated with 1,5-DCQA with and without stress-induced premature senescence with 150 µM $H_2O_2$. These genes are involved in cell cycle regulation and mitochondrial stress responses. Challenge with a near lethal level of oxidant stress typically induces an increase in SIRT2 and decrease in SIRT3 expression. The compound 1,5-DCQA induced a significant decrease in SIRT2 expression without stress. This is indicative of each having a potential for stimulating cell proliferation in the absence of oxidant challenge. 1,5-DCQA induced an increase in SIRT3 expression following oxidant challenge, indicating that it has a superior protective effect on the cells.

Table 2 below shows a summary of the data obtained to generate the results shown in FIGS. 2 to 7.

TABLE 2

| Expression of P16 | | | | | |
|---|---|---|---|---|---|
| | HPRT | P16 | dCt | ddct (1.275) | Relative Expression |
| media | 27.90031 | 29.17546 | 1.275 | 0.000 | 1.000 |
| stress | 28.55117 | 28.17046 | −0.381 | −1.656 | 3.151 |
| 1,5-DCQA | 26.33103 | 27.65584 | 1.325 | 0.050 | 0.966 |
| 1,5-DCQA & stress | 27.33624 | 28.09219 | 0.756 | −0.519 | 1.433 |

| Expression of P21 | | | | | |
|---|---|---|---|---|---|
| | HPRT | P21 | dCt | ddct (−3.761) | Relative Expression |
| media | 27.90031 | 24.13934 | −3.761 | 0.000 | 1.000 |
| stress | 28.55117 | 22.6142 | −5.937 | −2.176 | 4.519 |
| 1,5-DCQA | 26.33103 | 22.40333 | −3.928 | −0.167 | 1.122 |
| 1,5-DCQA & stress | 27.33624 | 21.31201 | −6.024 | −2.263 | 4.801 |

| Expression of SIRT2 | | | | | |
|---|---|---|---|---|---|
| | HPRT | SIRT2 | dCt | ddct (−0.016) | Relative Expression |
| media | 27.90031 | 27.91659 | 0.016 | 0.000 | 1.000 |
| stress | 28.55117 | 28.96023 | 0.409 | 0.393 | 0.762 |
| 1,5-DCQA | 26.33103 | 27.16427 | 0.833 | 0.817 | 0.568 |
| 1,5-DCQA & stress | 27.33624 | 27.72334 | 0.387 | 0.371 | 0.773 |

| Expression of SIRT3 | | | | | |
|---|---|---|---|---|---|
| | HPRT | SIRT3 | dCt | ddct (−2.079) | Relative Expression |
| media | 27.90031 | 29.97938 | 2.079 | 0.000 | 1.000 |
| stress | 28.55117 | 30.96285 | 2.412 | 0.333 | 0.794 |

TABLE 2-continued

| | | | | |
|---|---|---|---|---|
| 1,5-DCQA | 26.33103 | 28.55774 | 2.227 | 0.148 | 0.903 |
| 1,5-DCQA & stress | 27.33624 | 29.29568 | 1.959 | −0.120 | 1.086 |

Expression of XRCC5

| | HPRT | XRCC5 | dCt | ddct (−1.292) | Relative Expression |
|---|---|---|---|---|---|
| media | 27.90031 | 26.60795 | −1.292 | 0.000 | 1.000 |
| stress | 28.55117 | 26.09751 | −2.454 | −1.162 | 2.237 |
| 1,5-DCQA | 26.33103 | 25.48349 | −0.848 | 0.444 | 0.735 |
| 1,5-DCQA & stress | 27.33624 | 25.90307 | −1.433 | −0.141 | 1.103 |

Expression of hPOT1

| | HPRT | HPOT1 | dct | ddct (−1.835) | Relative Expression |
|---|---|---|---|---|---|
| media | 27.90031 | 29.73482 | 1.835 | 0.000 | 1.000 |
| stress | 28.55117 | 29.6853 | 1.134 | −0.701 | 1.625 |
| 1,5-DCQA | 26.33103 | 29.47246 | 3.141 | 1.306 | 0.404 |
| 1,5-DCQA & stress | 27.33624 | 29.5758 | 2.240 | 0.405 | 0.755 |

The results shown in Table 2 and FIGS. 2 to 7 were generated using the polymerase chain reaction (PCR), wherein the dCt and ddCT values are results used in statistical analysis. The abbreviation dCt relates to "delta cycle threshold" and the abbreviation ddCt relates to "delta delta cycle threshold". In these experiments, HPRT (hypoxanthine phosphoribosyltransferase, a protein from the HPRT-1 gene) was used as a control.

The results indicate that 1,5-DCQA has desirable properties as a protective agent during cell stress. This compound therefore protects mitochondria from stress, as determined by the level of SIRT 3 expression. The mode of action of this compound is understood to be downstream of p21 and appears to influence telomere biology in a positive fashion following oxidative insult. The results indicate that in normal fibroblasts, the compound (1,5-DCQA) down regulates SIRT2 expression by approximately 52%, but up regulates SIRT3 expression by approximately 36% in senescent fibroblasts. Thus, the results shown in Table 2 and in FIGS. 2 to 7 illustrate the beneficial properties of the composition. Advantageously, use of the composition does not completely inhibit the expression of SIRT2, since some SIRT2 expression is required for 'housekeeping' activities within the cell.

Figure 8:
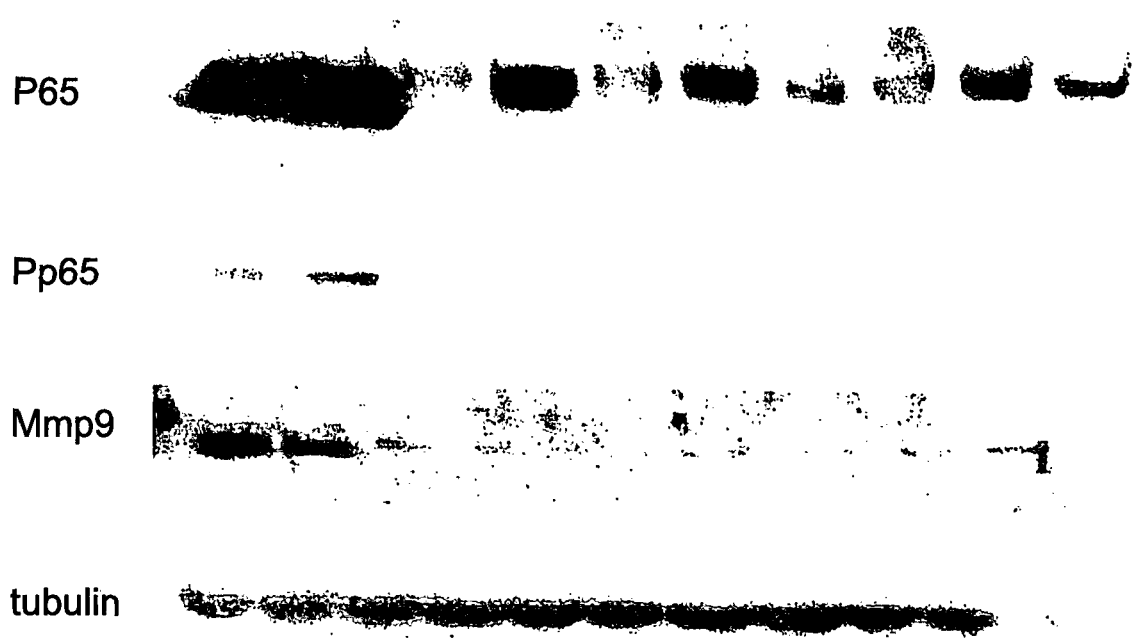
FIG. 8 shows the results of the effect of 1,4-Dicaffeoylquinic acid on p65 inhibition.

FIG. 8 shows the results of a Western blot which was performed on 50 μg of extracts from LNCaP cells and probed for p65, p65 (ser 536) and MMP-9 expression. Lanes 1 and 2 of the Western blot show the expression levels Hela control lysates comprising TNF-alpha (TNFα), in stimulated and unstimulated conditions. Lanes 3 and 4 show the results of LNCaP cell extracts, in stimulated and unstimulated conditions. In this case, the vehicle used is ethanol. Lanes 5 to 10 show the results of LNCaP cell extracts incubated for 24 hours in 0.1, 1, 3, 10, 30, 100 μM of 1,4-DCQA, respectively. Tubulin (50kD) was used as a loading control. P65 and Pp65 are known to be part of the NF-kappa B gene. These results show the effect of 1-4-Dicaffeoylquinic acid on p65 inhibition.

Figure 9:
FIG. 9 shows the results of the effect of 1,5-Dicaffeoylquinic acid on p65 inhibition.

FIG. 9 shows the results of a Western blot which was performed on 50 μg of extracts from LNCaP cells and probed for p65, Pp65 (ser 536) and MMP-9 expression. Lanes 1 and 2 of the Western blot show the expression levels Hela control lysates comprising TNF-alpha (TNFα), in stimulated and unstimulated conditions. Lanes 3 and 4 show the results of LNCaP cell extracts, in stimulated and unstimulated conditions. In this case, the vehicle used is ethanol. Lanes 5 to 10 show the results of LNCaP cell extracts incubated for 24 hours in 0.1, 1, 3, 10, 30, 100 μM of 1,5-DCQA, respectively. Tubulin (50kD) was used as a loading control. The results show that 1,5-DCQA does not inhibit the expression of p65, but does inhibit the phosphorylation of p65. The inhibition of MMP-9 is also clearly demonstrated at 0.1 μM to 100 μM.

The invention claimed is:

1. A method for the amelioration and/or treatment of disorders and diseases involving pre-mature, induced, or accelerated cell, tissue, or organ senescence comprising:
    administering a composition to a subject having premature, induced, or accelerated senescence associated degeneration in cells, tissues and/or organs, wherein the composition comprises:
    (a) 1,4-dicaffeoylquinic acid or 3,4,5-tricaffeoylquinic acid or an isomer or salt thereof and (b) at least one acceptable carrier,
    wherein the disorders and diseases are osteoporosis, osteopenia, periodontitis, intervertebral disc degeneration, side effects of radiotherapy, side effects of chemotherapy, alopecia, progeria, prostate cancer, breast cancer, stroke, atherosclerosis, or arteriosclerosis.

2. The method of claim 1, wherein the composition inhibits the activity of MMP-9.

3. The method of claim 1, wherein the method enhances extracellular matrix cohesion of the skin, and/or stimulates the biosynthesis of fibrillar collagens, elastin and/or fibrillins, and/or inhibits breakdown of elastin and/or collagenase type IV.

4. The method of claim 1, wherein the method ameliorates, and/or treats a condition associated with a loss of skin elasticity, reduces skin redness, reduces appearance of telangiectases, delays appearance of fine lines, and/or reduces appearance of dark circles around eyes.

5. The method of claim 1, wherein the method ameliorates, and/or treats a disorder or disease associated with an increase in the expression of the sirtuin 2 gene or protein, and/or a decrease in expression of the sirtuin 3 gene or protein.

6. The method of claim 1, wherein the method activates the expression of the sirtuin 3 gene to enhance the production of the sirtuin 3 protein, and/or the method inhibits the expression of the sirtuin 2 gene to inhibit the production of the sirtuin 2 protein.

7. The method of claim 1, wherein the composition inhibits expression of the p16INK4a gene.

8. The method of claim 1, wherein the method reverses senescence associated with degeneration of cells.

9. The method of claim 1, wherein the method ameliorates, and/or treats a disorder or disease associated with senescence of the hair and/or hair follicles.

10. The method of claim 1, wherein the method ameliorates, and/or treats a pathological disorder associated with senescence of cells or tissues.

11. The method of claim 1, wherein the method ameliorates, and/or treats a condition associated with senescence in endothelial cells.

12. The method of claim 1, wherein the composition is a plant extract.

13. The method of claim 1, wherein the step of administering the composition is further defined as administering the composition in combination with an adjuvant treatment.

14. The method of claim 1, wherein the composition is incorporated in a food or drink.

15. The method of claim 1, wherein the subject is a mammal or a human.

16. The method of claim 1, wherein the method reverses senescence associated with degeneration of stem cells and cells of the nervous system, tissues and/or organs.

17. The method of claim 1, wherein the composition is incorporated in a cosmetic composition.

18. The method of claim 1, wherein the method ameliorates, and/or treats side effects of radiotherapy or side effects of chemotherapy.

19. The method of claim 1, wherein the method maintains or extends the viability of organs, cells, or stem cells, before and/or after a process of transplantation, and/or in cell lines.

20. The method of claim 1, wherein the composition further comprises anti-cancer therapies.

21. A method for the amelioration and/or treatment of disorders and diseases involving accelerated senescence comprising:
 administering a composition to a subject having accelerated senescence associated degeneration in cells and tissues of the skin, hair follicles, nervous systems and/or eyes, wherein the composition comprises:
 (a) 1,4-dicaffeoylquinic acid or 3,4,5-tricaffeoylquinic acid or an isomer or salt thereof and (b) at least one acceptable carrier chosen from a vesicle, micelle, liposome, nanoparticle or combinations thereof
 wherein the disorders and diseases are side effects of radiotherapy or side effects of chemotherapy.

22. A method for the amelioration and/or treatment of disorders and diseases involving accelerated senescence comprising:
 administering a composition to a subject having accelerated senescence associated degeneration in cells and tissues of the hair follicles, nervous systems and/or eyes, wherein the composition comprises:
 (a) 1,4-dicaffeoylquinic acid or 3,4,5-tricaffeoylquinic acid or an isomer or salt thereof and (b) at least one acceptable carrier chosen from a vesicle, micelle, liposome, nanoparticle or combinations thereof
 wherein the disorders and diseases are side effects of radiotherapy, detrimental effects of radiation, or side effects of chemotherapy.

* * * * *